United States Patent
Kaushikkar et al.

(10) Patent No.: US 7,062,092 B2
(45) Date of Patent: Jun. 13, 2006

(54) SYSTEM, METHOD, AND COMPUTER SOFTWARE PRODUCT FOR GAIN ADJUSTMENT IN BIOLOGICAL MICROARRAY SCANNER

(75) Inventors: Shantanu V. Kaushikkar, San Jose, CA (US); Nathan K. Weiner, Stoughton, MA (US); Eric E. McKenzie, Malden, MA (US); John C. Stephens, Boulder Creek, CA (US)

(73) Assignee: Affymetrix, Inc., Santa Clara, CA (US)

( * ) Notice: Subject to any disclaimer, the term of this patent is extended or adjusted under 35 U.S.C. 154(b) by 584 days.

(21) Appl. No.: 09/682,071

(22) Filed: Jul. 17, 2001

(65) Prior Publication Data

US 2002/0168094 A1 Nov. 14, 2002

Related U.S. Application Data

(60) Provisional application No. 60/226,999, filed on Aug. 22, 2000, and provisional application No. 60/286,578, filed on Apr. 26, 2001.

(51) Int. Cl.
G06K 9/74 (2006.01)

(52) U.S. Cl. .................................................... 382/213
(58) Field of Classification Search ................. 382/312; 341/139; 348/255, 229.1, 230.1, 231.99
See application file for complete search history.

(56) References Cited

U.S. PATENT DOCUMENTS

| | | | | | |
|---|---|---|---|---|---|
| 4,016,557 | A | * | 4/1977 | Zitelli et al. ................. | 341/139 |
| 4,218,733 | A | * | 8/1980 | Maselli .......................... | 700/37 |
| 4,525,741 | A | * | 6/1985 | Chahal et al. ............... | 348/255 |
| 4,573,069 | A | * | 2/1986 | Lewis, Jr. .................... | 348/646 |
| 5,030,924 | A | * | 7/1991 | Fritz ........................... | 330/256 |
| 5,420,731 | A | * | 5/1995 | Thomas et al. ........... | 360/77.13 |
| 5,532,874 | A | | 7/1996 | Stein | |
| 6,072,624 | A | | 6/2000 | Dixon et al. | |
| 6,078,390 | A | | 6/2000 | Bengtsson | |
| 6,090,555 | A | | 7/2000 | Fiekowsky et al. | |
| 6,342,927 | B1 | * | 1/2002 | Kimoto et al. ............... | 348/569 |
| 6,349,144 | B1 | | 2/2002 | Shams | |
| 6,650,364 | B1 | * | 11/2003 | Itani et al. ................ | 348/229.1 |
| 6,679,844 | B1 | * | 1/2004 | Loftman et al. ............ | 600/443 |
| 6,741,124 | B1 | * | 5/2004 | Lucas .......................... | 330/59 |
| 6,750,906 | B1 | * | 6/2004 | Itani et al. ................ | 348/229.1 |
| 2002/0047853 | A1 | | 4/2002 | Bartell | |

FOREIGN PATENT DOCUMENTS

| | | |
|---|---|---|
| DE | 39 15 692 A | 11/1990 |
| WO | WO 99/47964 | 9/1999 |

OTHER PUBLICATIONS

Axon Instruments, Inc. Press Release dated Mar. 8, 2000 entitled, "Axon Instruments Announces Release of GenePix Pro 3.0", http://www.axon.com/press/pr20000308.htm.

(Continued)

*Primary Examiner*—Jose L. Couso
(74) *Attorney, Agent, or Firm*—William R McCarthy, III; Philip L. McGarrigle; Alan B. Sharr

(57) ABSTRACT

Systems, methods, and computer program products are described for adjusting the gain of a scanner. The scanner includes one or more excitation sources, an emission detector having a first gain, and a variable gain element having a second gain. One described method includes receiving a user-selected gain value, adjusting the first gain based on a first portion of the user-selected gain value, and adjusting the second gain based on a second portion of the user-selected gain value. Another described method includes selecting an auto-gain value, adjusting the first gain based on a first portion of the auto-gain value, adjusting the second gain based on a second portion of the auto-gain value, causing the scanner to collect sample pixel intensity values, determining a comparison measure based on comparing the sample pixel intensity values to desired pixel intensity values, and adjusting the auto-gain value based on the comparison measure.

48 Claims, 16 Drawing Sheets

OTHER PUBLICATIONS

GenePix Pro 3.0 Software, http://www.apbiotech.com/application/miroarray/GenePix_Pro3.htm.

Khan J. et al.; "DNA Microarray Technology: the anticipated impact on the study of human disease"; BIOCHIMICA ET BIOPHYSICA ACTA, Amsterdam, NL; vol. 1423, No. 2; Mar. 25, 1999; pp. M17–M28.

Xiang C. C.; "cDNA Microarry Technology and its Applications"; BIOTECHNOLOGY ADVANCES, Elsevier Publishing, Barking GB; vol. 18, No. 1; Mar. 2000; pp. 35–46.

Cortese J. D.; "Array of Options: Instrumentation to Exploit the DNA Microarray Explosion"; SCIENTIST, Institute for Scientific Information, US; vol. 14, No. 11; May 29, 2000; pp. 1–4.

Bowtell D. D. L.; "Options Available–From Start to Finish–For Obtaining Expression Data by Microarray"; NATURE GENETICS, NY, NY, US; vol. 21, No. SUPPL; Jan. 1999; pp. 25–32.

* cited by examiner

SYSTEM, METHOD, AND COMPUTER SOFTWARE PRODUCT FOR GAIN ADJUSTMENT IN BIOLOGICAL MICROARRAY SCANNER

CROSS REFERENCE TO RELATED APPLICATIONS

The present application relates to and claims priority from U.S. Provisional Patent Application Ser. No. 60/226,999, titled "System, Method, and Product for Linked Window Interface," filed Aug. 22, 2000, and U.S. Provisional Patent Application Ser. No. 60/286,578, titled "System, Method, and Product for Scanning of Biological Materials," filed Apr. 26, 2001, which are hereby incorporated herein by reference in their entireties for all purposes. The present application also relates to U.S. patent application Ser. No. 09/682,074 entitled System, Method, and Computer Program Product for Specifying a Scanning Area of a Substrate, and to U.S. patent application Ser. No. 09/682,076 entitled System, Method, and Computer Software Product for Grid Alignment of Multiple Scanned Images, both of which are filed concurrently herewith and are hereby incorporated herein by reference in their entireties for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF INVENTION

1. Field of the Invention

The present invention relates to systems, methods, and products for scanning arrays of biological materials and, more particularly, for amplifying, analyzing, and displaying information obtained from scanning.

2. Related Art

Synthesized probe arrays, such as Affymetrix® GeneChip® arrays, have been used to generate unprecedented amounts of information about biological systems. For example, a commercially available GeneChip® array set from Affymetrix, Inc. of Santa Clara, Calif., is capable of monitoring the expression levels of approximately 6,500 murine genes and expressed sequence tags (EST's).

Experimenters can quickly design follow-on experiments with respect to genes, EST's, or other biological materials of interest by, for example, producing in their own laboratories microscope slides containing dense arrays of probes using the Affymetrix® 417™ Arrayer or other spotting devices. Analysis of data from experiments with synthesized and/or spotted probe arrays may lead to the development of new drugs and new diagnostic tools. In some conventional applications, this analysis begins with the capture of fluorescent signals indicating hybridization of labeled target samples with probes on synthesized or spotted probe arrays. The devices used to capture these signals often are referred to as scanners, an example of which is the Affymetrix® 428™ Scanner from Affymetrix, Inc. of Santa Clara, Calif. There is a great demand in the art for methods for organizing, accessing and analyzing the vast amount of information collected by scanning microarrays. Computer-based systems and methods have been developed to assist a user to visualize the vast amounts of information generated by the scanners. These commercial and academic software applications typically provide such information as intensities of hybridization reactions or comparisons of hybridization reactions. This information may be displayed to a user in graphical form.

SUMMARY OF INVENTION

In accordance with some embodiments of the present invention, a computer program product is described for adjusting the gain of a scanner. The scanner includes one or more excitation sources, an emission detector having a first gain, and a variable gain element having a second gain. The computer program product, when executed on a computer system, performs a method including: (a) providing a user interface that enables a user to select a gain value; (b) receiving the user-selected gain value; (c) adjusting the first (or second) gain based, at least in part, on a first portion of the user-selected gain value; and (d) adjusting the second (or first) gain based, at least in part, on a second portion of the user-selected gain value. The word adjusting in this context includes increasing, decreasing, or leaving unchanged. The word gain includes amplification of a signal (i.e., a positive gain) and reduction of a signal (i.e., a gain less than one).

In some implementations of these embodiments, step (c) includes (i) determining the first portion to be equal to a no-change value when the user-selected gain value is equal to or less than a threshold value, and (ii) determining the first portion to be equal to an excess of the user-selected gain value over the threshold value, when the user-selected gain value is greater than the threshold value. Also in these implementations, step (d) includes the steps of (i) determining the second portion to be equal to the user-selected gain value when the user-selected gain value is equal to or less than a threshold value, and (ii) determining the second portion to be equal to the threshold value when the user-selected gain value is equal to or greater than the threshold value. The term no-change value means a value indicating that no change should be made to the associated gain, i.e., the first gain in these implementations. The threshold value may be predetermined.

One advantage of using this computer program product is that the user simply provides a gain value, which may be a single value, and the product allocates the user-selected gain between the emission detector and the variable gain element. That is, in some implementations, this allocation may be made without user involvement. In addition to simplifying the procedure for the user, this arrangement provides the user-selected gain while optimizing the signal to noise ratio achieved at all gain settings. For example, this optimization may be achieved because the program allocates gain based on the operational characteristics of the emission detector. In some emission detectors, for instance, the signal to noise ratio may be good at low gain settings but decline at higher gains. In such circumstances, the computer program product may allocate a first portion of a user-selected gain to be implemented by the variable gain element, such as a variable gain amplifier, that has good signal to noise performance over this first range of gains. If the user selects a gain that requires amplification outside of this first range, the computer program product allocates the additional portion of the user-selected gain (e.g., an amount greater than a threshold value based on the upper limit of the first range) to be implemented by the emission detector. The signal to noise ratio of the emission detector thus remains high because the detector is not pushed into its less desirable higher-gain range of operations. In typical applications, the performance characteristics of the emission detector and the variable gain element with respect to noise at various gains are known by the scanner manufacturer. In these applications, the threshold level at which the computer program product allocates additional gain to be delivered by the emission detector may be a predetermined level, i.e., determined by the computer program product based on a data value in a look up table or in accordance with another conventional technique. In alternative implementations, the user may select the threshold value.

In some implementations, the method performed by the computer program product may further include (e) receiving a calibration gain for a first of the one or more excitation sources. The calibration gain may be based, at least in part, on an output of the emission detector responsive to the first excitation source exciting a calibration source. In these implementations, the method also includes (f) adjusting the first gain, the second gain, or both based, at least in part, on the calibration gain.

In yet other implementations, the user interface further enables the user to associate the user-selected gain value with a first of one or more emission labels. Step (b) in these implementations includes receiving from the user interface the association of the user-selected gain value with the first emission label. Steps (c) and (d) are done when the first emission label is excited in a scanning operation. The method also includes, in other implementations, the additional step of (e) providing a second user interface that enables a user to initiate a scanning operation. In these implementations, step (b) includes (i) receiving the user-selected gain value from the first user interface and storing the user-selected gain value in a memory storage unit, and (ii) retrieving the user-selected gain value from the memory storage unit responsive to the user initiating a scanning operation. The first and second user interfaces may be the same interface, or may be included as elements of a common, i.e., the same, user interface.

In other embodiments, a computer program product for adjusting the gain of a scanner is described that, when executed on a computer system, performs a method including (a) receiving one or more user-selected gain values from one or more ranges of gain values (e.g., from one or more slide bars or other user-selectable graphical elements); (b) adjusting the gain of an emission detector of the scanner based, at least in part, on a first of the one or more user-selected gain values (e.g., a slide bar for control of the emission detector gain); and (c) adjusting the gain of a variable gain element of the scanner based, at least in part, on a second of the one or more user-selected gain values (e.g., a slide bar for control of the gain of the variable gain element). The method may also include (d) receiving a calibration gain for a first of the one or more excitation sources, wherein the calibration gain is based, at least in part, on an output of the emission detector responsive to the first excitation source exciting a calibration source; and (e) adjusting the first gain, the second gain, or both based, at least in part, on the calibration gain.

A gain adjustment system in accordance with other embodiments is described. The system includes a scanner that has one or more excitation sources, an emission detector having a first gain, and a variable gain element having a second gain. Also included in the system is a computer-implemented user interface that enables a user to select a user-selected gain value. Also included in the system is scanner control and analysis control logic comprising(i) a user-selected gain data manager that receives the user-selected gain value, and a scan gain controller that adjusts the first gain based, at least in part, on a first portion of the user-selected gain value, and that adjusts the second gain based, at least in part, on a second portion of the user-selected gain value.

In accordance with yet other embodiments, a method is described for adjusting the gain of a scanner. The method includes (a) receiving a user-selected gain value; (b) adjusting the gain of an emission detector of the scanner based, at least in part, on a first portion of the user-selected gain value; and (c) adjusting the gain of a variable gain element of the scanner based, at least in part, on a second portion of the user-selected gain value.

Various embodiments are also described with respect to auto gain operation. In one such embodiment, a computer program product adjusts the gain of a scanner that has one or more excitation sources, an emission detector having a first gain, and a variable gain element having a second gain. The computer program product, when executed on a computer system, performs a method including: (a) selecting an auto-gain value; (b) adjusting the first gain based, at least in part, on a first portion of the auto-gain value; c) adjusting the second gain based, at least in part, on a second portion of the auto-gain value; (d) causing the scanner to collect a plurality of sample pixel intensity values using the adjusted first and second gains; (e) determining a comparison measure based on comparing one or more of the plurality of sample pixel intensity values to one or more of a plurality of desired pixel intensity values; and (f) adjusting the auto-gain value based on the comparison measure. In these embodiments, steps (b) through (f) may be repeated until the comparison measure reaches an acceptance value or range, or until a number of repetitions exceeds an attempt number. In some implementations, the comparison measure may include a histogram of the plurality of sample pixel intensity values. The comparison measure may also, or alternatively, include a statistical measure.

A gain adjustment system is also described that includes a scanner having (i) one or more excitation sources, (ii) an emission detector having a first gain, and (iii) a variable gain element having a second gain. The system also includes scanner control and analysis control logic comprising a scan gain controller. The scan gain controller (i) selects an auto-gain value, (ii) adjusts the first gain based, at least in part, on a first portion of the auto-gain value;(iii) adjusts the second gain based, at least in part, on a second portion of the auto-gain value;(iv) causes the scanner to collect a plurality of sample pixel intensity values using the adjusted first and second gains; (v) determines a comparison measure based on comparing one or more of the plurality of sample pixel intensity values to one or more of a plurality of desired pixel intensity values; and (vi) adjusts the auto-gain value based on the comparison measure.

In yet another embodiment, a method is described for adjusting the gain of a scanner having one or more excitation sources, an emission detector having a first gain, and a variable gain element having a second gain. The method includes (a) selecting an auto-gain value; (b) adjusting the first gain based, at least in part, on a first portion of the auto-gain value; (c) adjusting the second gain based, at least in part, on a second portion of the auto-gain value; (d) causing the scanner to collect a plurality of sample pixel intensity values using the adjusted first and second gains; (e) determining a comparison measure based on comparing one or more of the plurality of sample pixel intensity values to one or more of a plurality of desired pixel intensity values; and(f) adjusting the auto-gain value based on the comparison measure.

Also described in accordance with some embodiments is a method including: (a) receiving a user-selected gain value; (b) applying a first gain to the emission signal based, at least in part, on a first portion of the user-selected gain value; and (c) applying a second gain to the emission signal based, at least in part, on a second portion of the user-selected gain value. A further embodiment is a method for adjusting an emission signal including: (a) selecting an auto-gain value; (b) applying a first gain to the emission signal based, at least in part, on a first portion of the auto-gain value;(c) applying a second gain to the emission signal based, at least in part, on a second portion of the auto-gain value; (d) determining a plurality of sample pixel intensity values based on the emission signal having applied to it the first and second gains; (e) determining a comparison measure based on comparing one or more of the plurality of sample pixel intensity values to one or more of a plurality of desired pixel intensity values; and (f) adjusting the auto-gain value based on the comparison measure.

Also, a computer program product is described in some embodiments that includes a gain-value receiver that receives a user-selected gain value; a first gain controller that applies a first gain to the emission signal based, at least in part, on a first portion of the user-selected gain value; and a second gain controller that applies a second gain to the emission signal based, at least in part, on a second portion of the user-selected gain value. In other embodiments, a computer program product includes an auto-gain value selector; a first gain controller that applies a first gain to the emission signal based, at least in part, on a first portion of the auto-gain value; a second gain controller that applies a second gain to the emission signal based, at least in part, on a second portion of the auto-gain value; an intensity manager that determines a plurality of sample pixel intensity values based on the emission signal having applied to it the first and second gains; a comparison manager that determines a comparison measure based on comparing one or more of the plurality of sample pixel intensity values to one or more of a plurality of desired pixel intensity values; and an auto-gain adjuster that adjusts the auto-gain value based on the comparison measure.

In another embodiment, a gain adjustment system is described that includes a scanner having one or more excitation sources, an emission detector having a first gain, and a variable gain element having a second gain. The system also includes a scan gain controller that adjusts the first and second gains.

The above embodiments and implementations are not necessarily inclusive or exclusive of each other and may be combined in any manner that is non-conflicting and otherwise possible, whether they be presented in association with a same, or a different, aspect of the invention. The description of one embodiment or implementation is not intended to be limiting with respect to other embodiments or implementations. Also, any one or more function, step, operation, or technique described elsewhere in this specification may, in alternative embodiments or implementations, be combined with any one or more function, step, operation, or technique described in the summary. Thus, the above embodiments and implementations are illustrative rather than limiting.

BRIEF DESCRIPTION OF DRAWINGS

The above and further features will be more clearly appreciated from the following detailed description when taken in conjunction with the accompanying drawings. In the drawings, like reference numerals indicate like structures or method steps and the leftmost one or two digits of a reference numeral indicates the number of the figure in which the referenced element first appears (for example, the element 125 appears first in FIG. 1, the element 1110 first appears in FIG. 11). In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

DETAILED DESCRIPTION

Figure 1:
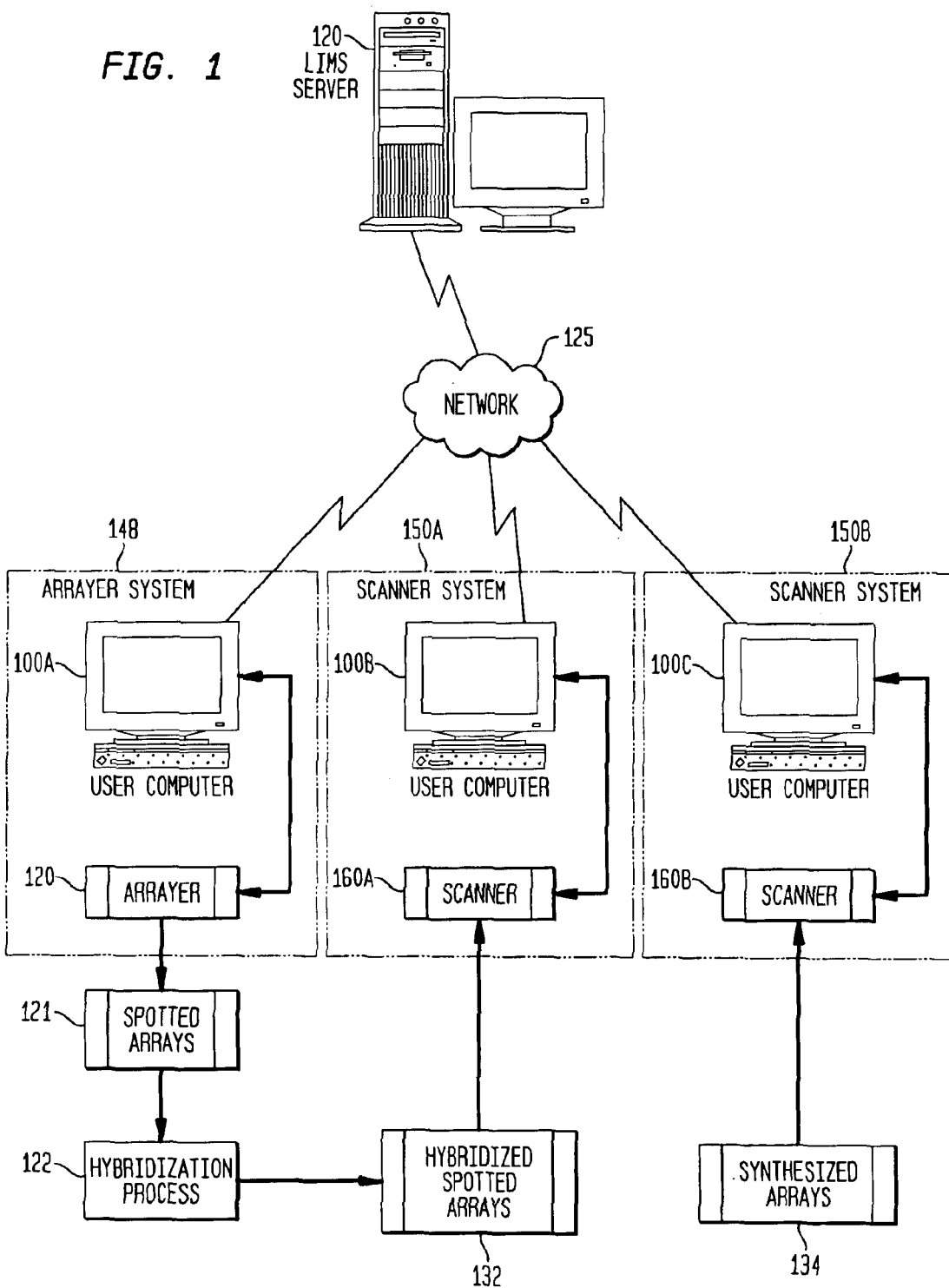
FIG. 1 is a simplified schematic diagram of one embodiment of networked systems for generating, sharing, and processing probe array data among computers on a network, including an arrayer system for generating spotted probe arrays and scanner systems for scanning spotted and synthesized probe arrays.

Systems, methods, and software products to acquire, process, analyze, and/or display data from experiments with synthesized and/or spotted arrays are described herein with respect to illustrative, non-limiting, implementations. Various other alternatives, modifications and equivalents are possible. For example, while certain systems, methods, and computer software products are described using exemplary embodiments with reference to spotted arrays analyzed using Affymetrix® scanners and/or Affymetrix software, the systems, methods, and products of the present invention are not so limited. For example, they generally may be applied with respect to many other probe arrays, including many types of parallel biological assays.

Probe Arrays

For example, certain systems, methods, and computer software products are described herein using exemplary implementations for acquiring, analyzing, and/or displaying data from arrays of biological materials produced by the Affymetrix® 417™ or 427™ Arrayer. Other illustrative implementations are referred to in relation to data from experiments with Affymetrix® GeneChip® arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, aspects of the systems, methods, and products described herein may, in some implementations, be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates, supports, or media (all or any of which may hereafter generally and collectively be referred to as substrates). Some implementations of synthesized arrays, their preparation, substrates, and the like are described in U.S. Pat. Nos. 5,744,305 and 5,445,934, which are hereby incorporated herein by reference in their entireties for all purposes. Moreover, with respect to some implementations in which the context so indicates or allows, the probes need not be immobilized in or on a substrate, and, if immobilized, need not be disposed in regular patterns or arrays. For convenience, the term probe array will generally be used broadly hereafter to refer to all of these types of arrays and parallel biological assays.

For convenience, an array made by depositing or positioning pre-synthesized or pre-selected probes on a substrate, or by depositing/positioning techniques that may be developed in the future, is hereafter referred to as a spotted array. Typically, but not necessarily, spotted arrays are commercially fabricated on microscope slides. These arrays often consist of liquid spots containing biological material of potentially varying compositions and concentrations. For instance, a spot in the array may include a few strands of short polymers, such as oligonucleotides in a water solution, or it may include a high concentration of long strands of polymers, such as complex proteins. The Affymetrix® 417™ and 427™ Arrayers, noted above, are devices that deposit densely packed arrays of biological material on a microscope slide in accordance with these techniques. Aspects of these, and other, spot arrayers are described in U.S. Pat. Nos. 6,121,048, 6,040,193 and 6,136,269, in PCT Applications Nos. PCT/US99/00730 (International Publication Number WO99/36760) and PCT/US 01/04285, in U.S. patent application Ser. Nos. 09/122,216, 09/501,099, and 09/862,177, and in U.S. Provisional Patent Application Ser. No. 60/288,403, all of which are hereby incorporated by reference in their entireties for all purposes. Other techniques for depositing or positioning biological probes on a substrate, i.e., creating spotted arrays, also exist. For example, U.S. Pat. No. 6,040,193 to Winkler, et al. is directed to processes for dispensing drops of biological material. The ''193 patent, and U.S. Pat. No. 5,885,837 to Winkler, also describe separating reactive regions of a substrate from each other by inert regions and spotting on the reactive regions. The ''193 and ''837 patents are hereby incorporated by reference in their entireties. Other techniques for producing spotted arrays are based on ejecting jets of biological material. Some implementations of the jetting technique use devices such as syringes or piezo electric pumps to propel the biological material.

Spotted arrays typically are used in conjunction with tagged biological samples such as cells, proteins, genes or EST''s, other DNA sequences, or other biological elements. These samples, referred to herein as targets, typically are processed so that they are spatially associated with certain probes in the probe array. In one non-limiting implementation, for example, one or more chemically tagged biological samples, i.e., the targets, are distributed over the probe array. Some targets hybridize with at least partially complementary probes and remain at the probe locations, while non-hybridized targets are washed away. These hybridized targets, with their tags or labels, are thus spatially associated with the targets'' complementary probes. The associated probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The ''832, ''992, ''138, and ''092 patents, and publication WO99/05323,are incorporated by reference herein in their entirety for all purposes.

To ensure proper interpretation of the term probe as used herein, it is noted that contradictory conventions exist in the relevant literature. The word probe is used in some contexts to refer not to the biological material that is deposited on a substrate, as described above, but to what has been referred to herein as the target. To avoid confusion, the term probe is used herein to refer to compounds such as those deposited on a substrate to create spotted arrays.

FIG. 1 is a simplified schematic diagram of illustrative systems for generating, sharing, and processing data derived from experiments using probe arrays (i e., spotted arrays and/or synthesized arrays). More particularly, an illustrative arrayer system 148 and illustrative scanner systems 150A and 150B (collectively, scanner systems 150) are shown. In this example, data may be communicated among user computer 100A of system 148, user computers 100B and 100C of systems 150, and Laboratory Information Management (LIMS) server 120 over network 125. LIMS server 120 and associated software generally provides data capturing, tracking, and analysis functions from a centralized infrastructure. Aspects of a LIMS are described in U.S. Provisional Patent Application Nos. 60/220,587 and 60/273,231, both of which are hereby incorporated by reference herein for all purposes. LIMS server 120 and network 125 are optional, and the systems in other implementations may include a scanner for spotted arrays and not synthesized arrays, or vice versa. Also, rather than employing separate user computers 100A and 100B to operate and process data from an arrayer and scanner, respectively, as in the illustrated implementation, a single computer may be used for all of these purposes in other implementations. More generally, a large variety of computer and/or network architectures and designs may be employed, and it will be understood by those of ordinary skill in the relevant art that many components of typical computer network systems are not shown in FIG. 1 for sake of clarity.

Arrayer 120

The illustrative system of FIG. 1 includes an arrayer 120 for producing spotted arrays, such as represented by spotted arrays 121. For example, arrayer 120 may be the Affymetrix® 417™ or 427™ Arrayer (commercially available from Affymetrix, Inc. of Santa Clara, Calif.), elements of which are hereafter described to provide an example of how arrayer 120 may operate in a commercial embodiment. As noted above, however, numerous variations are possible in the technologies and structures that may be used to produce spotted arrays, and thus it will be understood that the following description of arrayer 120 is merely illustrative, and is non-limiting.

Arrayer 120 of the illustrated implementation deposits spots on substrates consisting of standard glass microscope slides. The slides are held on a flat platen or cartridge (not shown) that registers the slides relative to a printing head (not shown) that is lowered and raised to effect spotting. The spotting elements of the printing head may include, for example, various numbers of Affymetrix® Pin-and-Ring™ mechanisms, as described, e.g., in U.S. patent application Ser. No. 09/862,177, or U.S. Provisional Patent Application Ser. No. 60/288,403, incorporated by reference above. For example, the printing head in illustrative implementations may accommodate 1, 4, 8, 12, 32 or 48 pairs of pin and ring elements to deposit the spots of biological material onto the slide. Arrayer 120 thus may in some implementations be capable of rapidly depositing many spots of biological fluids, such as would be useful in preparing large numbers of DNA microarrays. The ring of the Pin-and-Ring™ mechanism in one implementation includes a circular ring section formed from a circular piece of metal. The ring is attached at the end of an arm section that extends from a cylinder. The pin in this example is a single, rod-like device having at one end a very narrow tip. During operation, the pin is inserted into and through the cylinder with the tip being capable of moving freely through the opening of the ring.

In some implementations, fluids to be spotted onto the microscope slides may be stored in and retrieved from well plates (also commonly referred to as microtiter plates) having, for example a standard number of 96 or 348 wells. The well plates loaded with fluids may, in some implementations, be inserted by a user into a carousel included in arrayer 120. Arrayer 120 may include a robotic system having an effector arm that, under computer control, may be instructed to retrieve a well plate from the carousel. Arrayer 120 may, in some implementations, be capable of automatically identifying well plates. For example, machine readable indicators, e.g., bar codes, may be attached to the well plates and a bar code reader may be attached to the robotic system for reading the bar codes. The robotic system pivots the retrieved well plate from the carousel to a well plate retainer on the platen. In other implementations, a user may manually place slides on the platen.

Arrayer 120 further includes a robotic system that may be instructed, under computer control, to position the printing head with respect to the well plate in the well plate retainer in order to obtain fluids from the well plate for spotting. For example, as described in U.S. patent application Ser. No. 09/862,177, referred to above, rings of the printing head may be lowered into the wells of the well plate while the pins of the printing head remain out of contact with the fluids. The ring section is then raised out of the fluids. Given the design of the rings, an amount of the fluid is retained within the rings by the surface tension of the fluid and the surface activity of the inner walls of the rings. After the rings are raised out of the sample solution, the fluid held in each ring forms a convex meniscus that protrudes from the bottom opening of the ring. The printing head, including the rings with fluids, can then be positioned at a location above a substrate (i.e., microscope slide in this example) onto which a fraction of the fluid in each ring is to be deposited. The fluid volume in the ring is sufficient to deposit or spot more than one fraction. In fact, several hundred to a thousand or more fractions can be deposited from a single fluid volume retained in a ring. The number of fractions will depend on the desired volume of each fraction, the dimensions of the pin and the viscosity of the fluid.

Once the pin and ring mechanism is position over the desired location on the substrate, the tip of the pin is then lowered into, through and out of the fluid retained in the ring. The surface tension of the fluid retains the fluid within the ring while the pin penetrates into and moves through and out of the fluid. A fraction of the fluid is retained on the tip of the pin forming a meniscus. The portion of the pin that passes through the ring has a diameter that typically is small compared to the diameter of the ring, enabling the pin to pierce the fluid without breaking the meniscus and causing the fluid to leave the ring.

The pin with the fluid on the tip is lowered toward the surface of the substrate until the meniscus of the fluid on the end of the pin makes initial contact with the surface of the substrate. During typical operation, the pin contacts the substrate without damaging force. The fluid then adheres via surface tension to the surface of the substrate, and as the pin is raised, the fluid is transferred to the surface of the substrate by surface tension and gravity. The pin is moved back through and above the fluid in the ring. The process of sample deposition can then be repeated by repositioning the pin and ring mechanism at another desired location above the surface of the substrate. Alternatively, the pin and ring can be positioned over another, different surface.

In this exemplary implementation, the printing head is positioned on an x-y gantry that is capable of moving the printing head across the length and width of the platen, and thus over numerous slides retained on the platen. For example, the printing head may move in a serpentine manner from slide to slide along a column of slides arranged on the platen, and then back along an adjacent column of slides on the platen. The movement of the printing head may be controlled in accordance with various techniques such as using sensors to count markers and arrive at a preprogrammed destination. The printing head may optionally be directed under computer control to wash and dry stations to clean the pins and rings between spotting applications.

User Computer 100A

As shown in FIG. 1 and noted above, arrayer 120 operates in the illustrated implementation under computer control, e.g., under the control of user computer 100A. Although computer 100A is shown in FIG. 1 for clarity as being directly coupled to arrayer 120, it may alternatively be coupled to arrayer 120 over a local-area, wide-area, or other network, including an intranet and/or the Internet.

Figure 2:
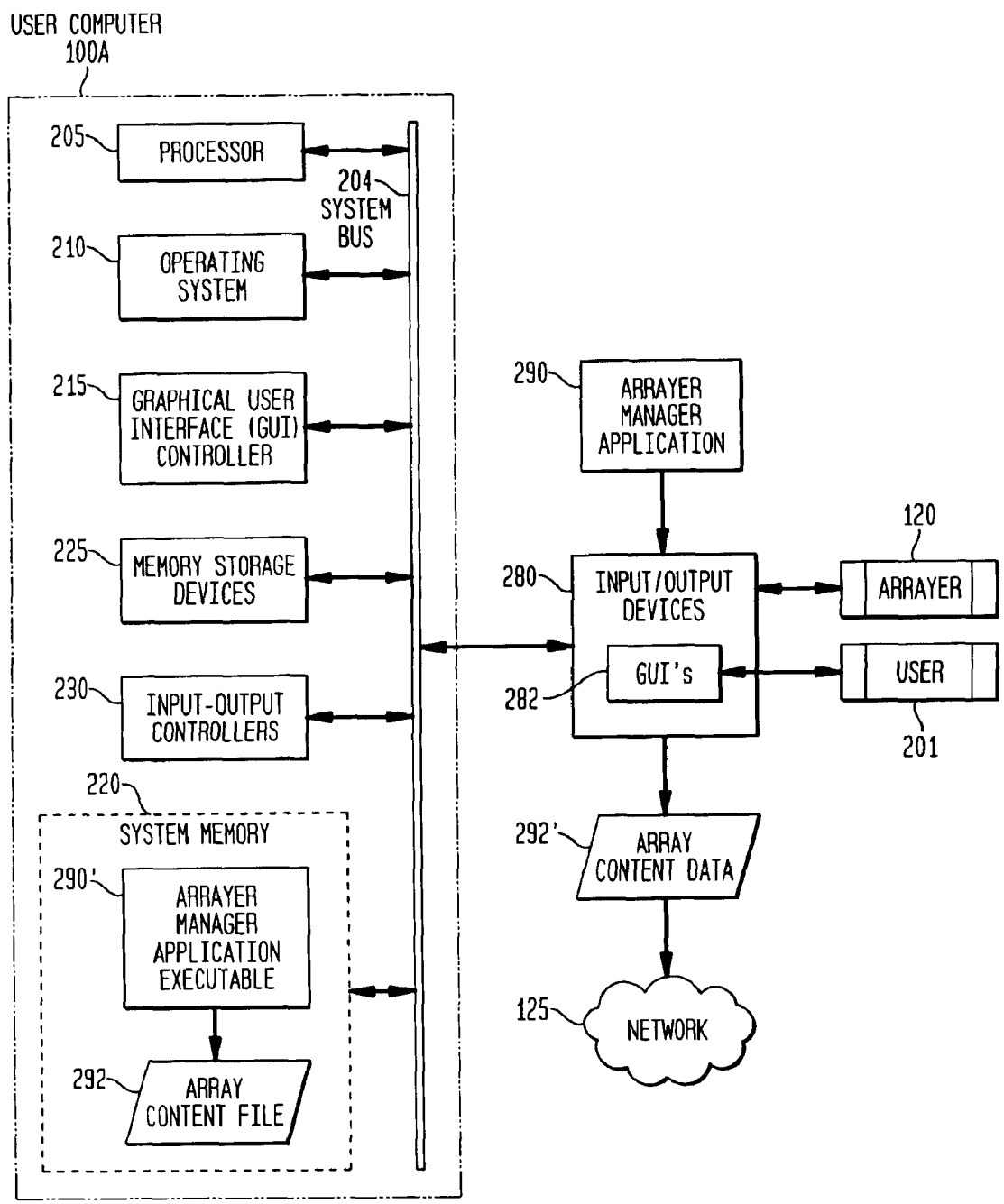
FIG. 2 is a functional block diagram of one embodiment of a user computer of the networked computers of FIG. 1 suitable for controlling the arrayer of FIG. 1 to produce spotted arrays.

FIG. 2 is a functional block diagram showing an illustrative implementation of computer 100A. Computer 100A may be a personal computer, a workstation, a server, or any other type of computing platform now available or that may be developed in the future. Typically, computer 100A includes known components such as processor (e.g., CPU) 205, operating system 210, system memory 220, memory storage devices 225, graphical user interface (GUI) controller 215, and input-output controllers 230, all of which typically communicate in accordance with known techniques such as via system bus 204. It will be understood by those skilled in the relevant art that there are many possible configurations of the components of computer 100A and that some components that may typically be included in computer 100A are not shown, such as cache memory, a data backup unit, and many other devices.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 230 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. GUI controller 215 may comprise any of a variety of known or future software programs for providing graphical input and output interfaces between computer 100A and a user 201 (e.g., an experimenter wishing to use arrayer 120 to generate spotted arrays), and for processing inputs from user 201 (hereafter sometimes referred to as user inputs or user selections).

Arrayer Manager Application 290

Arrayer manager application 290 of the illustrated implementation is a software application that controls functions of arrayer 120 and processes data supplied by user 201. As more particularly described with respect to certain implementations in U.S. Provisional Patent Application Ser. No. 60/288,403, incorporated by reference above, application 290, when executed in coordination with processor 205, operating system 210, and/or GUI controller 215, performs user interface functions, data processing operations, and data transfer and storage operations. For example, with respect to user interface functions, user 201 may employ one or more of GUI''s 282 to specify and describe particular clones and their location in particular wells of particular well plates. Using another of GUI''s 282, user 201 may specify how spots of the clones are to be arranged in arrays on one or more slides. Yet another of GUI''s 282 may be used to operate arrayer 120, e.g., to initiate the spotting of a number of slides without further user participation.

As will be evident to those skilled in the relevant art, application 290 may be loaded into system memory 220 and/or memory storage device 225 through an input device of devices 280. Alternatively, application 290 may be implemented as executable instructions stored in firmware. Executable code corresponding to application 290 is referred to as arrayer manager application executable 290' and is shown for convenience with respect to the illustrated implementation as stored in system memory 220. However, instructions and data including executable instructions of application 290, and data used or generated by it, may be located in or shifted among other memory devices, local or remote, as convenient for data storage, data retrieval, and/or execution.

Figure 3A:
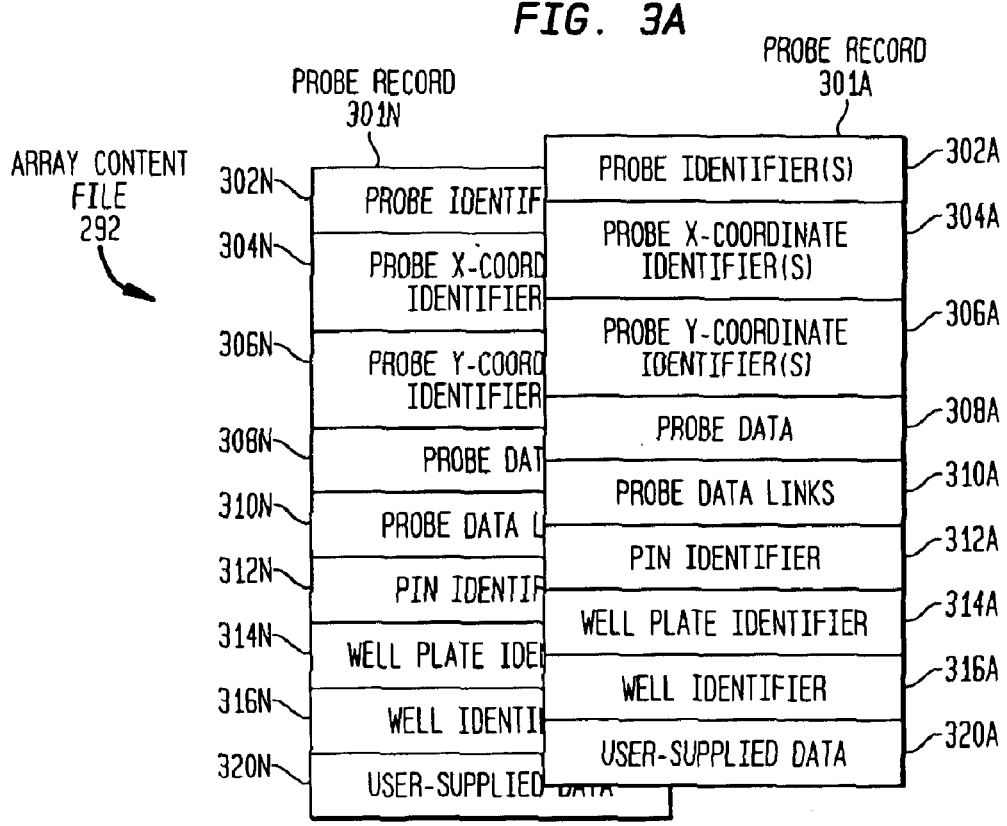
FIG. 3A is a graphical representation of data records in one embodiment of a data file suitable for storing data regarding spotted arrays produced in cooperation with the user computer of FIG. 2 and the arrayer of FIG. 1.
Figure 3B:
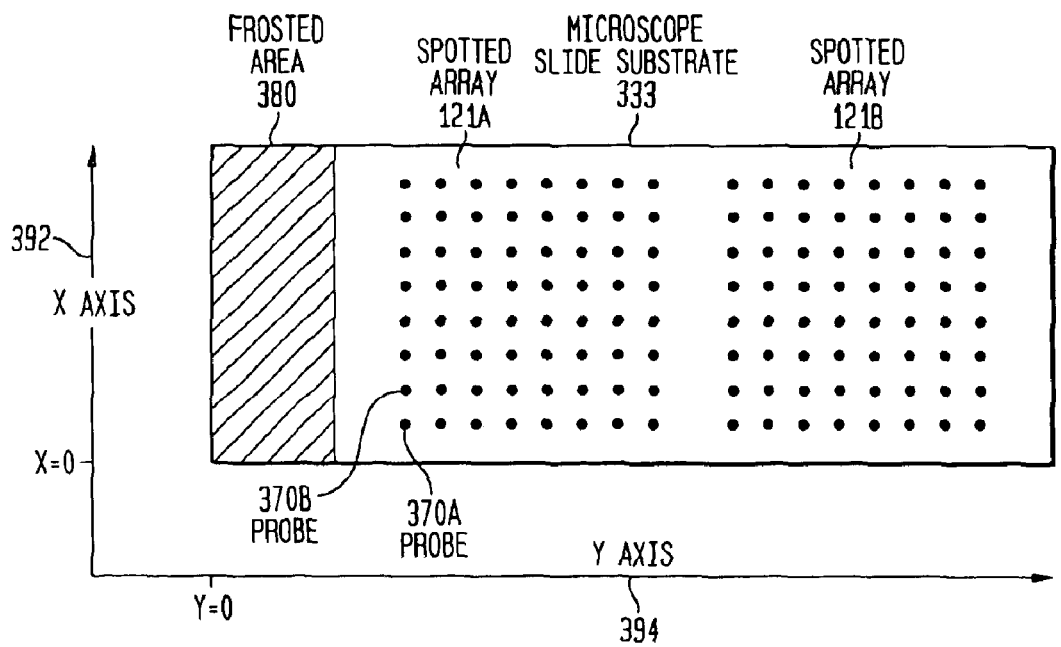
FIG. 3B is a graphical representation of a microscope slide including illustrative embodiments of spotted arrays produced in cooperation with the user computer of FIG. 2 and the arrayer of FIG. 1.

FIG. 3A is a graphical representation of illustrative data records in one implementation of a data file generated by arrayer manager application executable 290'. The data file in this illustration, referred to as array content file 292, consists of records 301, each one of which (i.e., records 301A through 301N for any number of N records) corresponds to one of N spots, i.e., probes, that have been deposited, or are planned to be deposited, on spotted arrays 121. For example, with reference to the graphical representation of spotted arrays 121 shown in FIG. 3B, two arrays 121A and 121B (collectively, arrays 121) have been printed on microscope slide substrate 333 by arrayer 120. Array 121A includes probe 370A. It is assumed for purposes of illustration that data relating to probe 370A is stored by executable 290' in probe record 301 A. In this example, each of the records in file 292 includes the following illustrative fields: probe identifier(s) 302, probe x-coordinate identifier(s) 304, probe y-coordinate identifier(s) 306, probe data 308, probe data links 310, pin identifier 312, well plate identifier 316, and user-supplied data 320.

The field in record 301A labeled probe identifier(s) 302A thus, in this example, includes certain information related to the identification of probe 370A. For instance, field 302A may include a name for cDNA deposited by a pin of arrayer 120 in array 121A to produce probe 370A. In various implementations, field 302A may also, or in addition, include a nucleotide identifier and/or a gene symbol that identifies probe 370A. Also, field 302A may include a build or release number of a database so that the data source used to develop the probe can be identified. As yet another example of information that may be included in field 302A, a probe may be identified as either an original or as a replicate. For instance, for quality control or other reasons, probe 370B of array 121A may be the same probe as probe 370A, or a number of such replicate probes may be deposited. The designation of original or replicate number assists in comparing results from probes that are based on the same sample. As one of ordinary skill in the relevant art will readily appreciate, all or some of this identifying data may be stored as a single value in field 302A (such as, for example, concatenating name, nucleotide identifier, etc.), in separate fields (e.g., 302A', 302A'', etc., not shown), in linked fields, and so on as may be convenient for data storage and/or processing. The other fields described below similarly are only representative of many possible storage and data retrieval architectures.

Field 308A, labeled probe data in this example, may include probe-related data such as the chromosome location of the gene or EST represented by the probe, the band location on the chromosome, a SNP or other type of marker that can identify the location on the chromosome, and so on. Field 310A, labeled probe data links in this example, similarly may include an accession number from GenBank, a UniGene cluster number, and/or another identifier that facilitates access to data related to probe 370A that is stored in a database. This database may, but need not, be external to computer 100A and accessed via network 125 and/or the Internet or other network. Systems for providing access to such information are described, for example, in U.S. Provisional Patent Application Ser. No. 60/288,429, hereby incorporated herein by reference in its entirety. Field 312A of this example identifies the pin on the print head(s) that is used to deposit probe 370A onto the slide. This information may be useful in comparing probes deposited with the same pin to determine, for example, if the pin is defective. Fields 314A and 316A contain information that respectively identifies the well plate and particular well from which biological fluid was taken to create probe 370A. Field 320A may contain a variety of data supplied by user 201 such as the user"s name, the data of the experiment, and so on. It will be understood that there are many other types of data relating to probe 370A that may be stored, and that numerous alternative arrangements may be implemented for storing them.

Scanner 160A: Optics and Detectors

Any of a variety of conventional techniques, or ones to be developed in the future, may be used to generate probe-target pairs in probe arrays that may be detected using a scanner. As one illustrative example that will be familiar to those of ordinary skill in the relevant art, conventional fluidics stations, hybridization chambers, and/or various manual techniques (as, for example, generally and collectively represented by hybridization process 122 in FIG. 1) may be used to apply one or more labeled targets to spotted arrays on microscope slides. In a particular implementation, for instance, sample of a first target may be labeled with a first dye (an example of what may more generally be referred to hereafter as an emission label) that fluoresces at a particular characteristic frequency, or narrow band of frequencies, in response to an excitation source of a particular frequency. A second target may be labeled with a second dye that fluoresces at a different characteristic frequency. The excitation source for the second dye may, but need not, have a different excitation frequency than the source that excites the first dye, e.g., the excitation sources could be the same, or different, lasers. The target samples may be mixed and applied to the probes of spotted arrays on microscope slides, and conditions may be created conducive to hybridization reactions, all in accordance with known techniques. In accordance with other techniques, such as typically are applied with respect to Affymetrix® GeneChip® synthesized arrays, samples of one labeled target are applied to one array and samples of a second labeled target are applied to a second array having the same probes as the first array. Hybridization techniques are applied to both arrays. For example, synthesized arrays 134 of FIG. 1 may be illustratively assumed to be two GeneChip® synthesized arrays that have been subject to hybridization processes with respect to two different target samples, each labeled with different fluorescent dyes. See, e.g., U.S. Pat. No. 6,114,122, which is hereby incorporated by reference herein in its entirety.

Many scanner designs may be used to provide excitation signals to excite labels on targets or probes, and to detect the emission signals from the excited labels. In references herein to illustrative implementations, the term excitation beam may be used to refer to light beams generated by lasers to provide the excitation signal. However, excitation sources other than lasers may be used in alternative implementations. Thus, the term excitation beam is used broadly herein. The term emission beam also is used broadly herein. As noted, a variety of conventional scanners detect fluorescent or other emissions from labeled target molecules or other material associated with biological probes. Other conventional scanners detect transmitted, reflected, or scattered radiation from such targets. These processes are sometimes generally and collectively referred to hereafter for convenience simply as involving the detection of emission beams. The signals detected from the emission beams are generally referred to hereafter as emission signals and this term is intended to have a broad meaning commensurate with that intended herein for the term emission beams.

Various detection schemes are employed depending on the type of emissions and other factors. A typical scheme employs optical and other elements to provide an excitation beam, such as from a laser, and to selectively collect the emission beams. Also generally included are various light-detector systems employing photodiodes, charge-coupled devices, photomultiplier tubes, or similar devices to register the collected emission beams. For example, a scanning system for use with a fluorescently labeled target is described in U.S. Pat. No. 5,143,854, hereby incorporated by reference in its entirety for all purposes. Other scanners or scanning systems are described in U.S. Pat. Nos. 5,578,832, 5,631,734, 5,834,758, 5,936,324, 5,981,956, 6,025,601, 6,141,096, 6,185,030, 6,201,639, 6,218,803, and 6,252,236; in PCT Application PCT/US99/06097 (published as WO99/47964); and in U.S. Provisional Patent Application Ser. No. 60/286,578, each of which also is hereby incorporated by reference in its entirety for all purposes.

Figure 4:
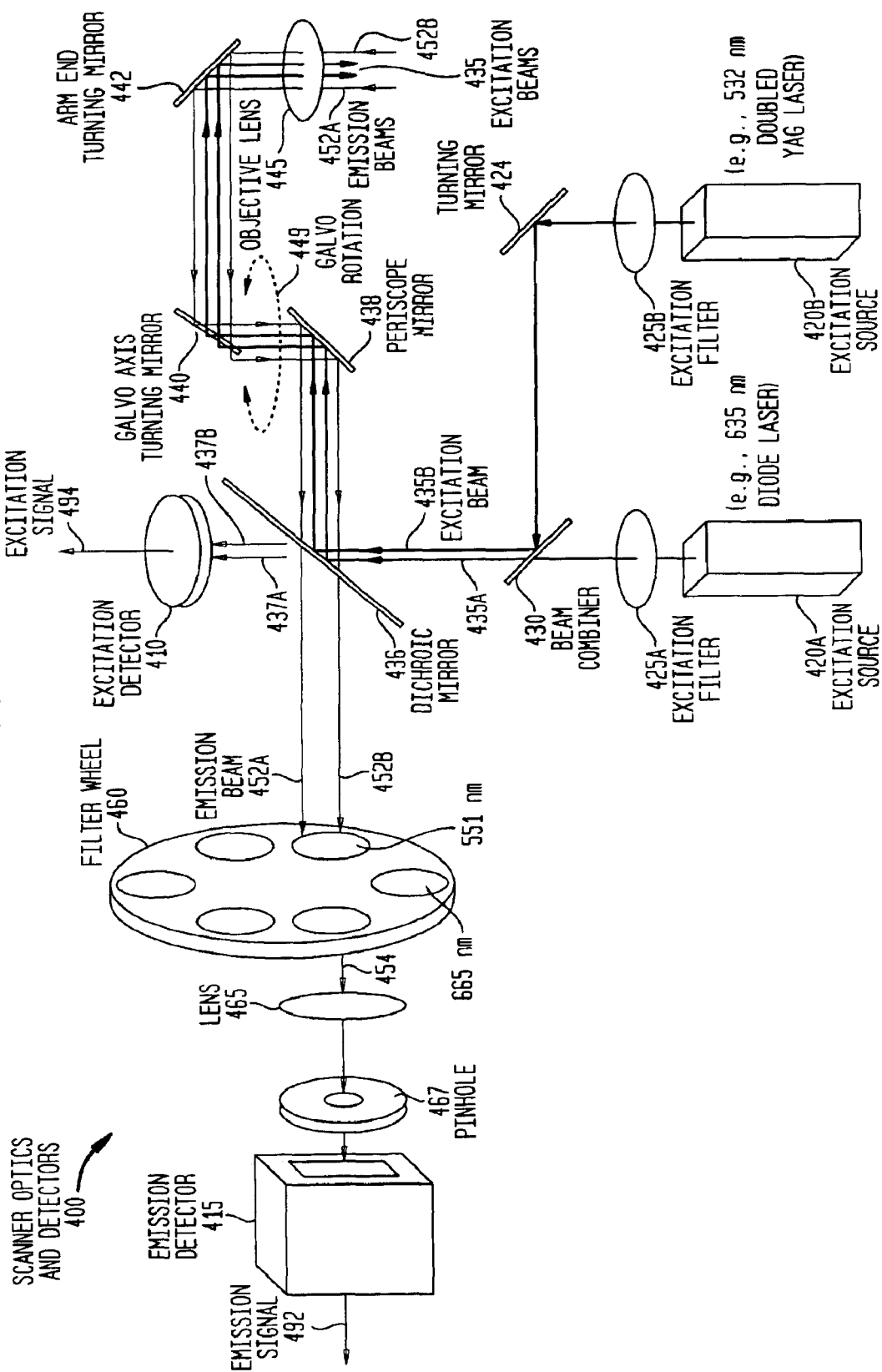
FIG. 4 is a simplified graphical representation of selected components of one embodiment of a scanner of FIG. 1 suitable for scanning arrays.

FIG. 4 is a simplified graphical representation of selected components of an illustrative type of scanner 160A suitable for scanning hybridized spotted arrays 132A and 132B disposed on slide 333 (i.e., in this example, spotted arrays 121A and 121B, respectively, after hybridization process 122). These illustrative components, which will be understood to be non-limiting and not exhaustive, are referred to collectively for convenience as scanner optics and detectors 400. Scanner optics and detectors 400 include excitation sources 420A and 420B (collectively referred to as excitation sources 420). Any number of one or more excitation sources 420 may be used in alternative embodiments. In the present example, sources 420 are lasers; in particular, source 420A is a diode laser producing red laser light having a wavelength of 635 nanometers and , source 420B is a doubled YAG laser producing green laser light having a wavelength of 532 nanometers. Further references herein to sources 420 generally will assume for illustrative purposes that they are lasers, but, as noted, other types of sources, eg. , x-ray sources, may be used in other implementations.

Sources 120A and 120B may alternate in generating their respective excitation beams 435A and 435B between successive scans, groups of successive scans, or between full scans of an array. Alternatively, both of sources 120 may be operational at the same time. For clarity, excitation beams 435A and 435B are shown as distinct from each other in FIG. 4. However, in practice, turning mirror 424 and/or other optical elements (not shown) typically are adjusted to provide that these beams follow the same path.

Scanner optics and detectors 400 also includes excitation filters 425A and 425B that optically filter beams from excitation sources 420A and 420B, respectively. The filtered excitation beams from sources 420A and 420B may be combined in accordance with any of a variety of known techniques. For example, one or more mirrors, such as turning mirror 424, may be used to direct filtered beam from source 420A through beam combiner 430. The filtered beam from source 420B is directed at an angle incident upon beam combiner 430 such that the beams combine in accordance with optical properties techniques well known to those of ordinary skill in the relevant art. Most of combined excitation beams 435 are reflected by dichroic mirror 436 and thence directed to periscope mirror 438 of the illustrative example. However, dichroic mirror 436 has characteristics selected so that portions of beams 435A and 435B, referred to respectively as partial excitation beams 437A and 437B and collectively as beams 437, pass through it so that they may be detected by excitation detector 410, thereby producing excitation signal 494.

Figure 5A:
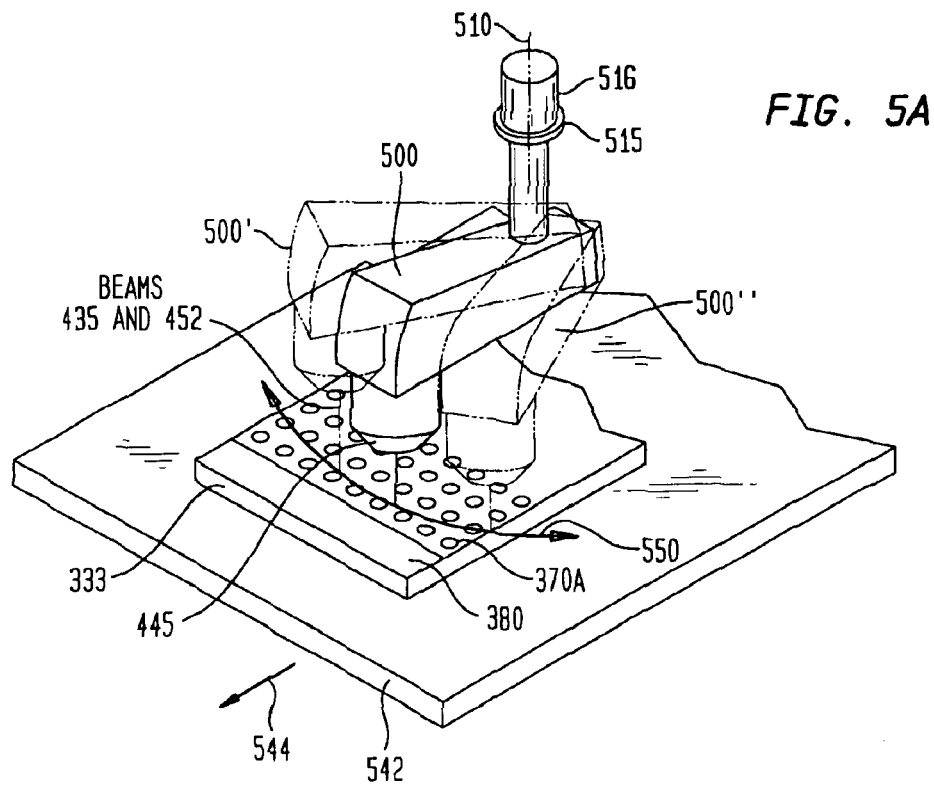
FIG. 5A is a perspective view of a simplified exemplary configuration of a scanning arm portion of the scanner of FIG. 4.
Figure 5B:
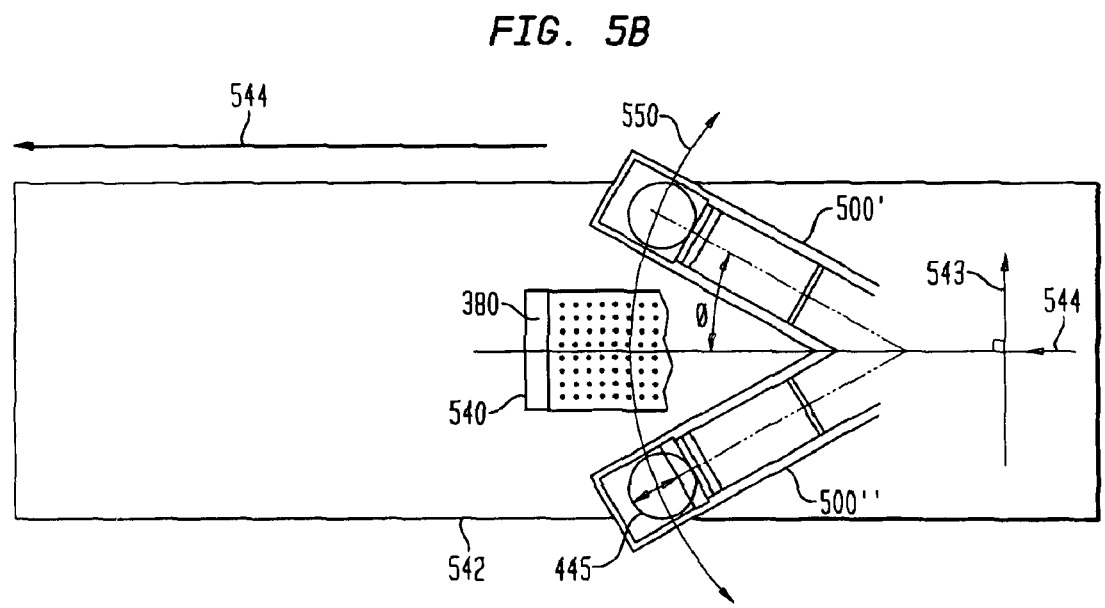
FIG. 5B is a top planar view of the scanning arm of FIG. 5A as it scans biological features on one embodiment of a spotted array being moved by a translation stage under the arm''s arcuate path.

In the illustrated example, excitation beams 435 are directed via periscope mirror 438 and arm end turning mirror 442 to an objective lens 445. As shown in FIGS. 5A and 5B, lens 445 in the illustrated implementation is a small, light-weight lens located on the end of an arm that is driven by a galvanometer around an axis perpendicular to the plane represented by galvo rotation 449 shown in FIG. 4. Objective lens 445 thus, in the present example, moves in arcs over hybridized spotted arrays 132 disposed on slide 333. Flourophores in hybridized probe-target pairs of arrays 132 that have been excited by beams 435 emit emission beams 452 (beam 452A in response to excitation beam 435A, and beam 452B in response to excitation beam 435B) at characteristic wavelengths in accordance with well known principles. Emission beams 452 in the illustrated example follows the reverse path as described with respect to excitation beams 435 until reaching dichroic mirror 436. In accordance with well known techniques and principles, the characteristics of mirror 436 are selected so that beams 452 (or portions of them) pass through the mirror rather than being reflected.

In the illustrated implementation, filter wheel 460 is provided to filter out spectral components of emission beams 452 that are outside of the emission band of the fluorophore, thereby providing filtered beams 454. The emission band is determined by the characteristic emission frequencies of those fluorophores that are responsive to the frequencies of excitation beams 435. In accordance with techniques well known to those of ordinary skill in the relevant arts, including that of confocal microscopy, filtered beams 454 may be focused by various optical elements such as lens 465 and also passed through illustrative pinhole 467 or other element to limit the depth of field, and thence impinges upon emission detector 415.

Emission detector 415 may be a silicon detector for providing an electrical signal representative of detected light, or it may be a photodiode, a charge-coupled device, a photomultiplier tube, or any other detection device that is now available or that may be developed in the future for providing a signal indicative of detected light. For convenience of illustration, detector 415 will hereafter be assumed to be a photomultiplier tube (PMT). Detector 415 thus generates emission signal 492 that represents numbers of photons detected from filtered emission beam 454.

FIG. 5A is a perspective view of a simplified representation of the scanning arm portion of scanner optics and detectors 400. Arm 500 moves in arcs around axis 510, which is perpendicular to the plane of galvo rotation 449. A position transducer 515 is associated with galvanometer 515 that, in the illustrated implementation, moves arm 500 in bi-directional arcs. Transducer 515, in accordance with any of a variety of known techniques, provides an electrical signal indicative of the radial position of arm 500. Certain non-limiting implementations of position transducers for galvanometer-driven scanners are described in U.S. Pat. No. 6,218,803, which is hereby incorporated by reference in its entirety for all purposes. The signal from transducer 515 is provided in the illustrated implementation to user computer 100B so that clock pulses may be provided for digital sampling of emission signal 492 when arm 500 is in certain positions along its scanning arc.

Arm 500 is shown in alternative positions 500' and 500" as it moves back and forth in scanning arcs about axis 510. Excitation beams 435 pass through objective lens 445 on the end of arm 500 and excite fluorophore labels on targets hybridized to certain of probes 370 in arrays 132 disposed on slide 333, as described above. The arcuate path of excitation beams 435 is schematically shown for illustrative purposes as path 550. Emission beams 452 pass up through objective lens 445 as noted above. Slide 333 of this example is disposed on translation stage 542 that is moved in what is referred to herein as the y direction 544 so that arcuate path 550 repeatedly crosses the plane of arrays 132.

FIG. 5B is a top planar view of arm 500 with objective lens 445 scanning arrays 132 as translation stage 542 is moved under path 550. As shown in FIG. 5B, arcuate path 550 of this example is such that arm 500 has a radial displacement of $\theta$ in each direction from an axis parallel to direction 544. What is referred to herein as the x direction, perpendicular to y-direction 544, is shown in FIG. 5B as direction 543. Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030 and 6,201,639, all of which have been incorporated by reference above. It will be understood that although a galvanometer-driven, arcuate, scanner is described in this illustrative implementation, many other designs are possible, such as the voice-coil-driven scanner described in U.S. patent application Ser. No. 09/383,986, hereby incorporated herein by reference in its entirety for all purposes.

Figure 6A:
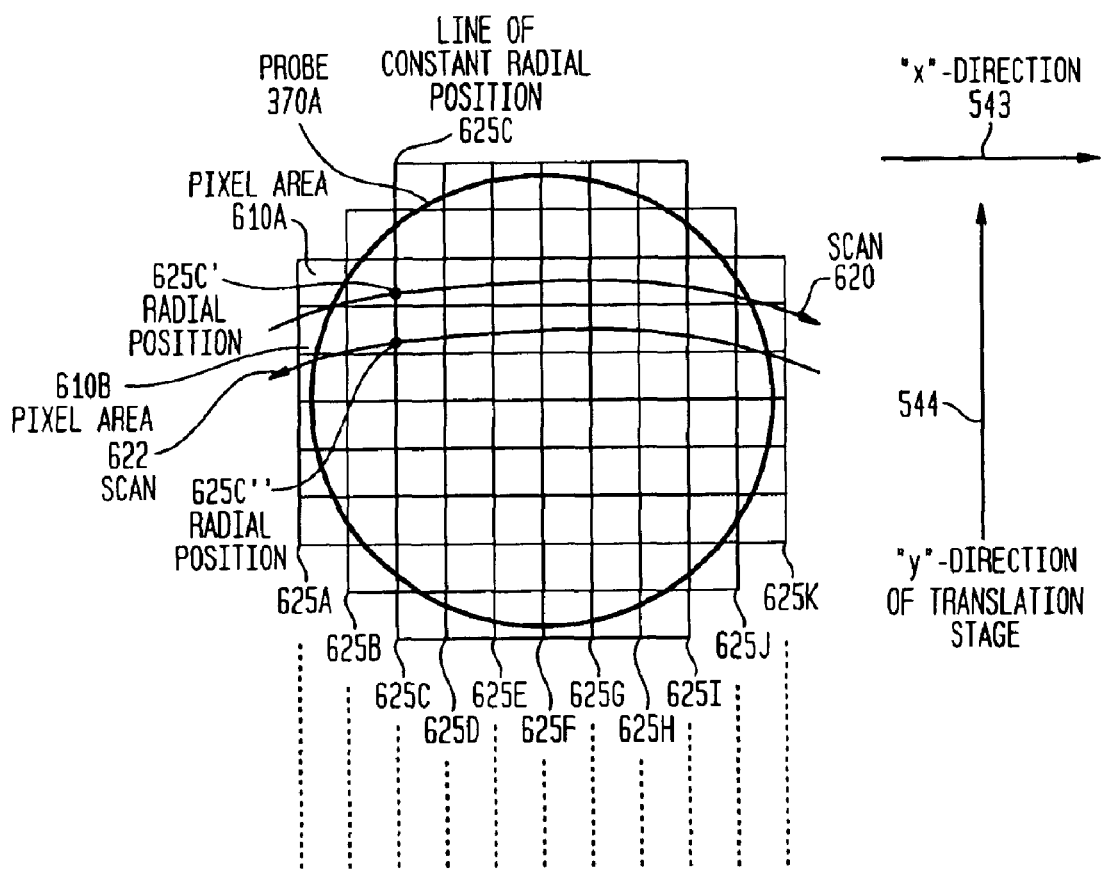
FIG. 6A is a graphical representation of one embodiment of a probe feature showing bidirectional scanning lines such as may be implemented using the scanning arm of FIGS. 5A and 5B.

FIG. 6A is a simplified graphical representation of illustrative probe 370A as it is scanned by scanner 160A. It is assumed for illustrative purposes that probe 370A has hybridized with a fluorescently labeled target. Although FIG. 6A shows probe 370A in idealized form, i.e. a perfect circle, it will be understood that many shapes, including irregular shapes, are possible.

In the manner described above, objective lens 445 scans over probe 370A (and other probes of arrays 132) in bi-directional arcs. An illustrative scan 620 is shown in FIG. 6A, which is not necessarily drawn to scale; e.g., the ratio of the radius of the arc of scan 620 to the radius of probe 370A is illustrative only. As also noted, probe 370A moves under objective lens 445 carried by translation stage 542 in y-direction 544. In particular, in the illustrated implementation, arm 500 scans in an arc in one direction, shown as left-to-right scan 620 in FIG. 6A. Translation stage 542 is then moved incrementally by a stepping motor (not shown) in y-direction 544 and arm 500 then scans back in the opposite direction, shown as right-to-left arcuate scan 622. Translation stage 542 is again moved in direction 544, and so on in scan-step-scan-step sequences. The distance between scans 620 and 622 thus corresponds to the distance that translation stage 542 is moved in each increment, although it will be understood that the distance shown in FIG. 6A is not necessarily to scale and is illustrative only. It will be understood that any other combination of scanning and stepping is possible in alternative implementations, and that scanning and moving of translation stage 542 may occur at the same or at overlapping times in some implementations. Translation stage 542 need not be stepped in some implementations, but may, for example, be moved continuously.

Figure 6B:
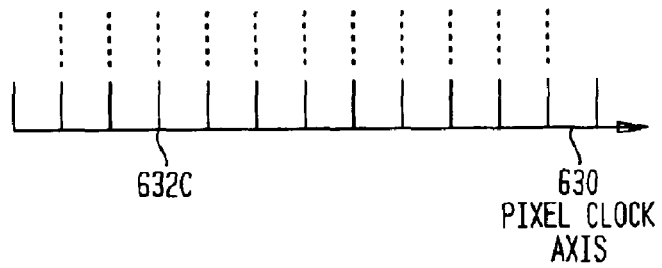
FIG. 6B is an illustrative plot of pixel clock pulses aligned with the scanned probe feature of FIG. 6A to show illustrative radial position sampling points.

FIG. 6B is a plot having a pixel clock axis 630 showing when clock pulses 632 occur. Clock pulses 632 may be generated by a pixel clock of scanner 160A (e.g., complex programmable logic device 830, described below) or, alternatively, they may be generated by software executing in computer 100B (e.g., executable 790', described below). Axis 630 in the illustrated implementation is a spatial axis; that is, each of clock pulses 632 occurs in reference to the radial location of arm 500 during each scan, as described in greater detail below. Thus, with reference to the position of translation stage 542 indicated by scan 620, a clock pulse 632A occurs prior to arm 500 passing over probe 370A from the left as shown in FIGS. 6A and 6B. (For sake of clarity of illustration only, vertical dotted lines are provided between FIGS. 6A and 6B, and between FIGS. 6B and 6C, to illustrate the alignment of these figures.) As another example, clock pulse 632C occurs with respect to scan 620 when arm 500 has just passed over portions of probe 370A indicated by pixel areas 610A and 610B. These areas are referred to as pixel areas because a digital value is assigned to each such area in the illustrated implementation based on the strength of a processed emission signal associated with that area. In accordance with known techniques, clock pulses 632 enable the digital sampling of the processed emission signal.

As noted, clock pulses 632 are spatially rather than temporally determined in the illustrated implementation. Moreover, in some aspects of the illustrated implementation, galvanometer 516 is driven by a control signal provided by user computer 100B such that the velocity of arm 500 in x-direction 444 is constant in time during those times when arm 500 is over probe 370A (and, typically, over other of probes 370 of arrays 132 as they are scanned). That is, dx/dt is a constant (and thus the angular velocity varies) over the probe-scanning portions of each arc and, in particular, it is a constant during the times when clock pulses are generated to enable digital sampling. As is evident, dx/dt must be reduced to zero between each successive scan, but this deceleration and reversal of direction takes place after arm 500 has passed over probe 370A (or, more generally, array 132A or 132B). The design and implementation of a galvanometer control signal to provide constant dx/dt are readily accomplished by those of ordinary skill in the relevant art.

Thus, the approximate sampling rate may readily be calculated based on the desired scanning speed (dx/dt) and desired pixel resolution. To provide an illustrative example, a spot deposited by an Affymetrix® 417™ or 427™ Arrayer typically has a diameter of approximately 150 to 200 microns. Spotted arrays made using these instruments typically may be deposited over a surface having a width of about 22 millimeters on a microscope slide that is 25 millimeters wide. In order to achieve pixel resolution of about 10 microns, a sampling rate of about 160 kHz is sufficient for scanning speeds typical for scanners used with respect to these probe arrays, such as the Affymetrix® 428™ scanner. Other sampling rates, readily determined by those of ordinary skill, may be used in other applications in which, for example, different scanning speeds are used and/or different pixel resolutions are desired. The desired pixel resolution typically is a function of the size of the probe features, the possibility of variation in detected fluorescence within a probe feature, and other factors.

Figure 6C:
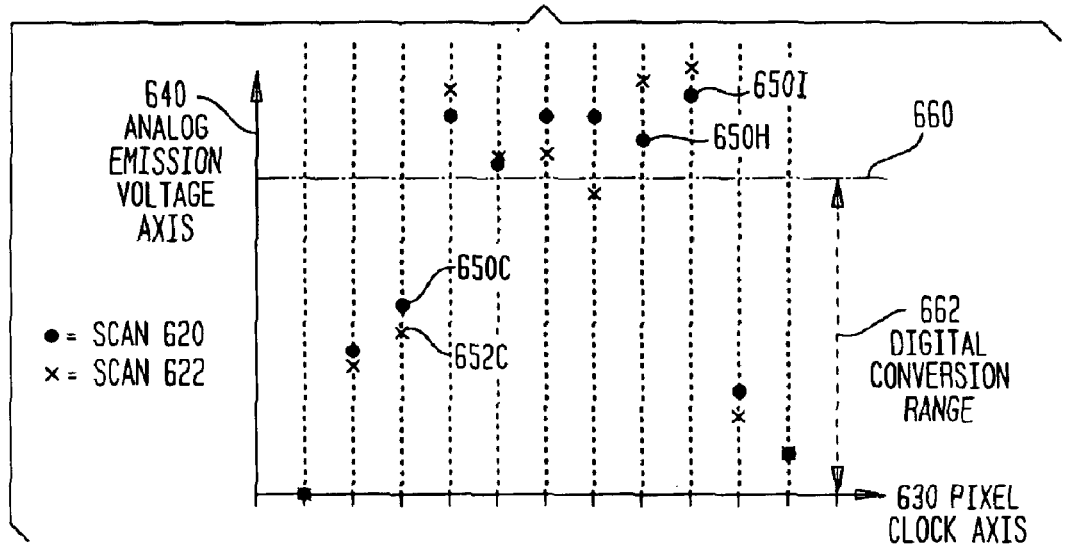
FIG. 6C is an illustrative plot of sampled analog emission voltages aligned with the pixel clock pulses of FIG. 6B.

FIG. 6C shows digital values representative of emission signal 492 as sampled at (and/or collected for an adjoining period before) points on scans 620 and 622 represented by constant radial position lines 625A-K (collectively referred to as radial position lines 625). The voltages sampled during scan 620 are shown as dots, while the voltages sampled during scan 622 are shown as x''s. The determination of when to initiate pixel clock signals may be made using position transducer 515, as described in greater detail in U.S. Provisional Patent Application Ser. No. 60/286,578, incorporated by reference above. Thus, for example, voltage 650C of FIG. 6C is representative of emission signal 492 based on sampling enabled by a pixel clock pulse at point 632C on axis 630 that is triggered when arm 500 is at radial position 625C during scan 620. After translation stage 542 has been incremented, voltage 652C is sampled during scan 622 at the same radial position, shown as radial position 625C''.

User Computer 100B

Figure 7:
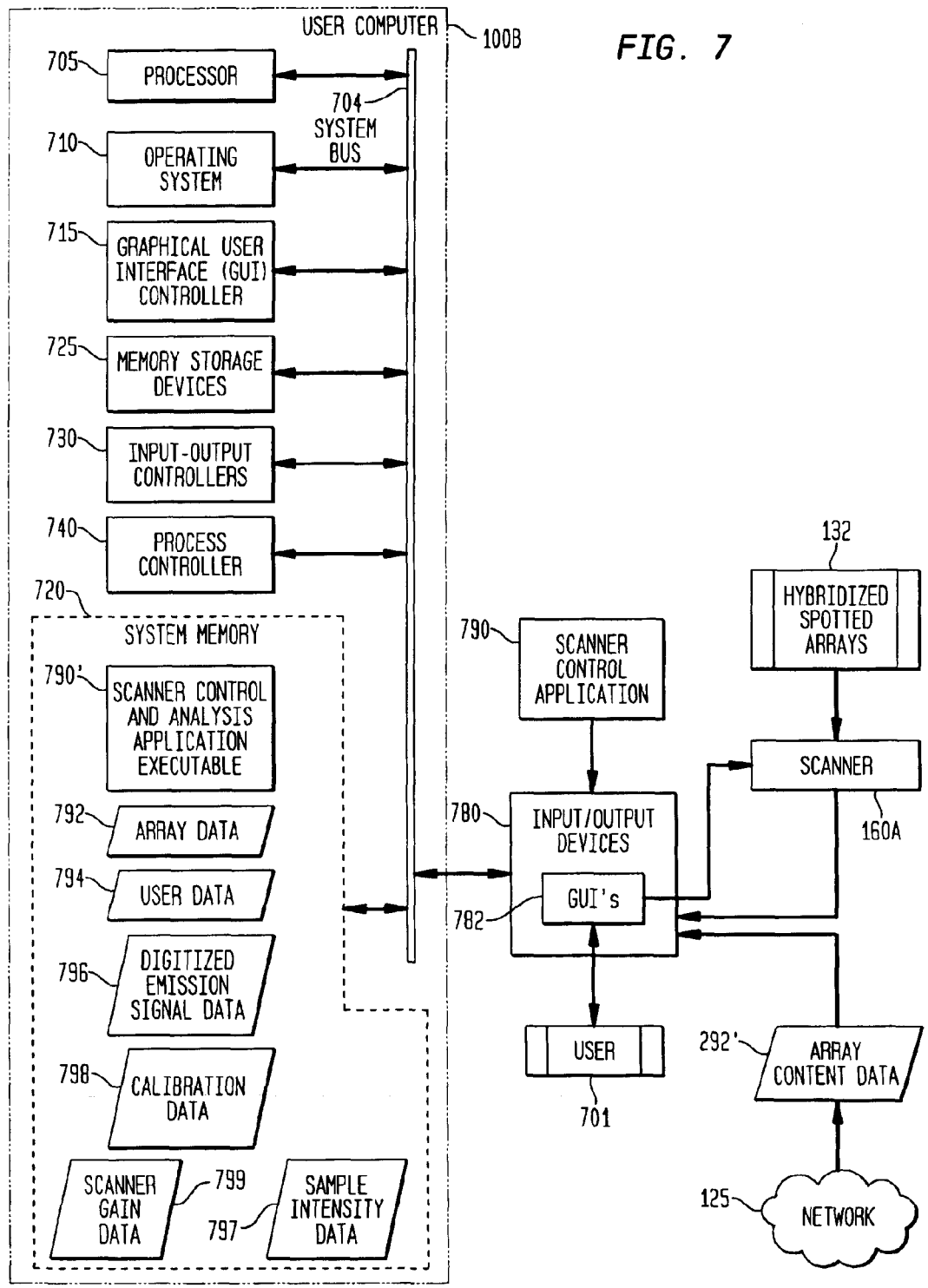
FIG. 7 is a functional block diagram of one embodiment of a scanner system of FIG. 1.

As shown in FIG. 1 and noted above, scanner 160B operates in the illustrated implementation under computer control, e.g., under the control of user computer 100B, as shown in greater detail in FIG. 7. Although computer 100B is shown in FIGS. 1 and 7 for clarity as being directly coupled to scanner 160A, it may alternatively be coupled to scanner 160A over a local-area, wide-area, or other network, including an intranet and/or the Internet. Computer 100B may be a personal computer, a workstation, a server, or any other type of computing platform now available or that may be developed in the future. Typically, computer 100B includes known components such as processor (e.g., CPU) 705, operating system 710, system memory 720, memory storage devices 725, GUI controller 715, and input-output controllers 730, all of which typically communicate in accordance with known techniques such as via system bus 704. It will be understood by those skilled in the relevant art that there are many possible configurations of the components of computer 100B and that some components that may typically be included in computer 100B are not shown, such as cache memory, a data backup unit, and many other devices.

Input-output controllers 730 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 730 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. Graphical user interface (GUI) controller 715 may comprise any of a variety of known or future software programs for providing graphical input and output interfaces between computer 100B and a user 701 (e.g. , an experimenter wishing to use scanner 160A to acquire and analyze information from spotted arrays), and for processing inputs from user 701 (hereafter sometimes referred to as user inputs or user selections). To avoid confusion, references hereafter to a GUI generally are directed to one or more graphical user interfaces displayed on a display device of devices 780 to user 701, such as GUI 782A of FIGS. 8 and 9, described below. To be distinguished are references to a GUI controller, such as GUI controller 715, that operates to display the GUI''s to user 701 and to process input information provided by user 701 through the GUI''s. As is well known in the relevant art, a user may provide input information using a GUI by selecting, pointing, typing, speaking, and/or otherwise operating, or providing information into, one or more input devices of devices 780 in a known manner.

Computer 100B may optionally include process controller 740 that may, for example, be any of a variety of PC-based digital signal processing (DSP) controller boards, such as the M44 DSP Board made by Innovative Integration of Simi Valley, Calif. More generally, controller 740 may be implemented in software, hardware or firmware, or any combination thereof.

Scanner control and analysis application 790 of the illustrated implementation is a software application that controls functions of scanner 160A. In addition, when executed in coordination with processor 705, operating system 710, GUI controller 715, and/or process controller 740, application 790 performs user interface functions, data and image processing operations, and data transfer and storage operations related to data provided by or to scanner 160A and/or user 701, as described in greater detail below. Affymetrix® Jaguar™ software, available from Affymetrix, Inc., is a commercial product that, in some implementations, includes various aspects of application 790.

As will be evident to those skilled in the relevant art, application 790 may be loaded into system memory 720 and/or memory storage device 725 through an input device of devices 780. Alternatively, application 790 may be implemented as executable instructions stored in firmware, or a combination of firmware and software. Executable code corresponding to application 790 is referred to as scanner control and analysis application executable 790' and is shown for convenience with respect to the illustrated implementation as stored in system memory 720. However, instructions and data including executable instructions of executable 790', and data used or generated by it, may be located in or shifted among other memory devices, local or remote, as convenient for data storage, data retrieval, and/or execution. The instructions of executable 790', also called computer control logic, when executed by processor 705, enable computer 100B to perform functions of the illustrated systems. Accordingly, executable 790' may be referred to as a controller of computer 100B. More specifically, in some implementations, the present invention includes a computer program product comprising a computer usable medium having control logic (computer software program, including program code) stored therein. In various embodiments, software products may be implemented using any of a variety of programming languages, such as Visual C++ or Visual Basic from Microsoft Corporation, Java™ from Sun Microsystems, Inc., and/or other high or lower level programming languages. The control logic, when executed by processor 705, causes processor 705 to perform some of the functions of the invention, as described herein. In other embodiments, some functions of the present invention may be implemented primarily in hardware using, for example, a hardware state machine. Implementation of the hardware state machine so as to perform the functions described herein will be apparent to those skilled in the relevant arts.

Gain Adjustment Components 890

Figure 8:
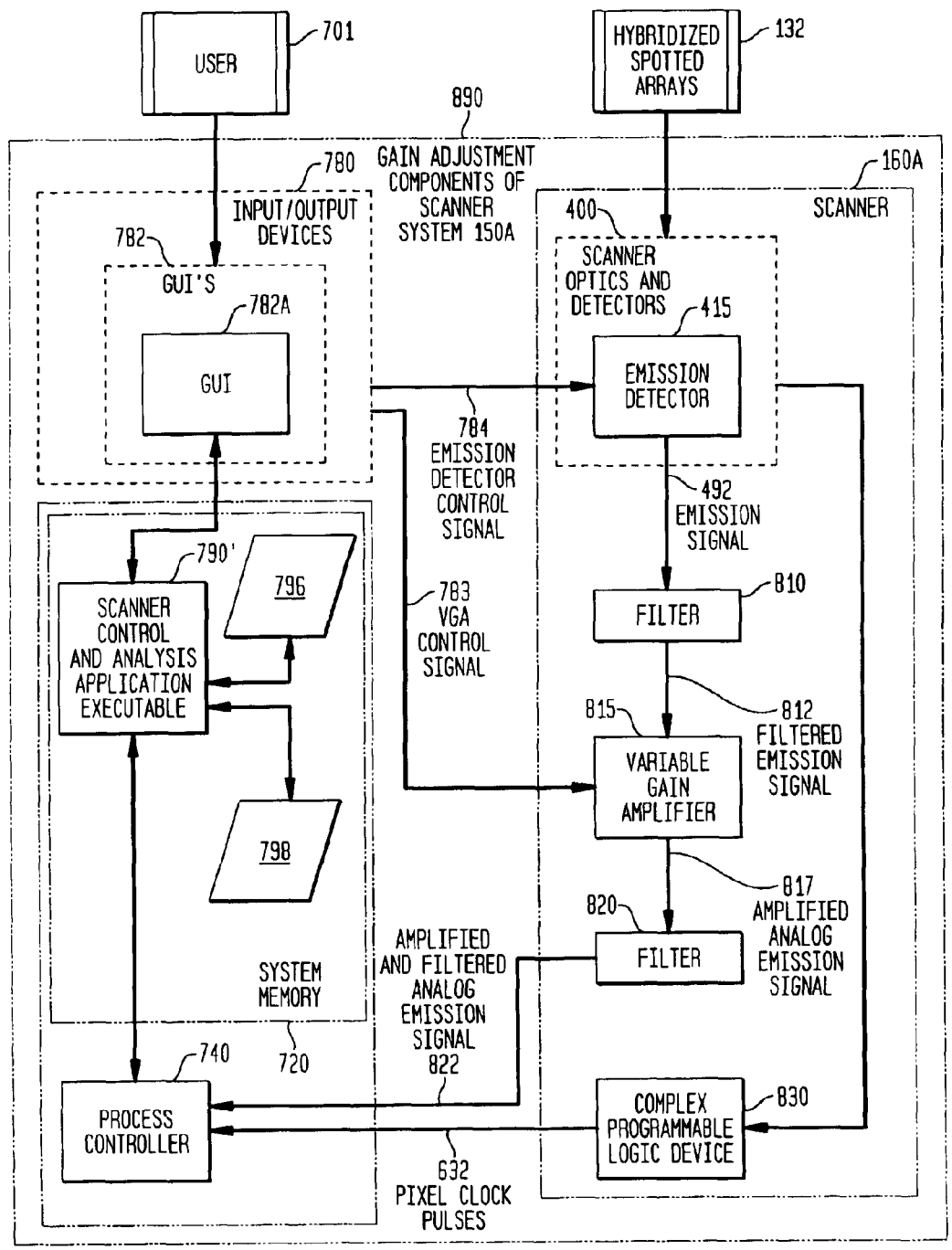
FIG. 8 is a simplified functional block diagram of one embodiment of selected elements of the scanner system of FIG. 7 comprising illustrative gain adjustment systems.

FIG. 8 is a simplified functional block diagram of one example of a configuration of gain adjustment components of illustrative scanner system 150A. For convenience of illustration, these components are described with reference to user computer 100B of FIGS. 1 and 7 and scanner 160B of FIGS. 1, 4, 5A, and 5B, although it will be understood that many alternative computer and/or scanner implementations are possible. For sake of clarity, FIG. 8 omits some aspects of computer 100B and scanner 160B as described above (e.g., communications among components of computer 100B via system bus 704), the functions of which are implicit in FIG. 8 and will be evident to those of ordinary skill in the relevant art.

A reason for providing gain adjustment is that, under certain conditions, the dynamic range of scanner 160B may be exceeded. For example, the dynamic range of scanner 160B may be exceeded due to excitation source 420A or 420B having been set at too high a gain, a higher-than-anticipated responsiveness of labels to excitation beams 435, a high gain setting of emission detector 415, a high gain setting of circuitry that amplifies emission signal 492 (e.g., variable gain amplifier 815, described below), or for other reasons. When the dynamic range is exceeded, some image pixels displayed to represent emission signal intensities may appear to be equally bright even though they represent emissions of varying intensities. This effect, whatever its cause, may interfere with the implementation of conventional techniques that, for example, search for the boundaries between bright and dim elements in an alignment pattern. The unintended result may be that an alignment grid is inaccurately positioned over an image because the grid was inaccurately aligned with an alignment pattern defined by boundaries between bright and dim pixels. See, e.g., U.S. patent application Ser. No. 09/681,819, hereby incorporated herein in its entirety for all purposes. Another unintended result may be that data regarding emission signal values is lost due to signal saturation.

Figure 6D:
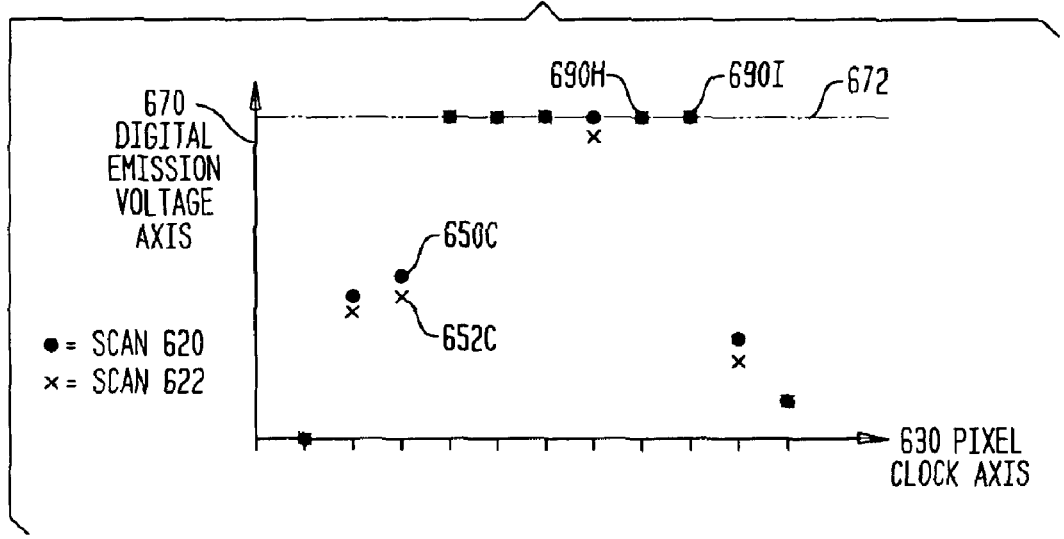
FIG. 6D is an illustrative plot of digital emission voltages corresponding to the analog emission voltages of FIG. 6C, including saturated values.

One example of a saturation effect is illustrated by FIGS. 6C and 6D. In FIG. 6C, analog voltage values of emission signal 492 (or amplified and/or filtered versions of that signal, as described below) are sampled by process controller 740 according to pixel clock pulses 632. The sampled analog voltages are shown on axis 640 of FIG. 6C, some of which (such as voltages 650I and 650H) are above a saturation value 660. Saturation value 660 typically is imposed because of limitations in digital conversion such as represented by digital conversion range 662. For example, it may be determined, based on desired resolution, anticipated dynamic range, and digital processing constraints, that analog voltages within range 662 will be converted to digital values between 0 and $2^{16} -1$, i.e., between 0 and 65,535. Analog voltages above value 660 would thus typically be represented by digital values 690H and 690I at the maximum digital conversion value represented by maximum digital voltage line 672. Specifically, in this example, the digital value both of values 690H and 690I is 65,535, even though corresponding analog voltages 650I and 650H have different values. It is also possible that hardware limitations, such as the range of power supplies in amplifier 815, described below, impose an analog saturation voltage such that voltages 650I and 650H would have a same value even though they represented emissions of different intensities. Similarly, emission detector 415 may saturate so that values of emission signal 492 are constant above a saturation value.

The gain adjustment components of scanner 160A, as shown in the illustrated implementation of FIG. 8, include emission detector 415, filters 810 and 820, variable gain amplifier 815, and CPLD 830. Emission detector 415 may be any of a variety of conventional devices including, for example, a photomultiplier tube (PMT), such as included in the HC 120 Series PhotoSensor Modules available from Hamamatsu Corporation USA of Bridgewater, N.J. VGA 815 is a type of what more generally is referred to as a variable gain element. VGA 815 may be any of a variety of conventional amplification devices such as the model AD603 amplifier available from Analog Devices of Norwood, Mass. CPLD 830 may be any conventional CPLD (or similar device such as a Field Programmable Gate Array), such as are available from Altera Corporation of San Jose, Calif., or other suppliers.

Filter 810 may be any filter designed to eliminate high frequency spikes that may be present in signal 492 and thus provide protection to VGA 815. As described in U.S. Provisional Patent Application Ser. No. 60/286,578 incorporated above, it generally is desirable for bidirectional scanning, such as in the illustrated implementation of FIGS. 4, 5A, 5B, and 6A, that the rise and fall response characteristics of emission signal filters be symmetrical. Thus, linear-phase filters, such as high-order Bessel filters, may advantageously be employed. In particular, filter 810 may be the first stage of a Bessel filter. Filter 820 may advantageously comprise additional Bessel filter stages having the desired response characteristics while providing low-pass filtering of noise in emission signal 492. As described in application 60/286,578, noise may be present due to the use of relatively inexpensive lasers such that noise in excitation beams 435 causes corresponding noise in emission beams 452.

CPLD 830 provides pixel clock pulses 632 to controller 740 so that, in accordance with known analog-to-digital techniques, it may sample analog emission signal 822. CPLD 830 determines clock pulses 632 in the illustrated implementation by comparing radial position information from galvo position transducer 515 with radial position data stored in system memory 220, as described in application 60/286,578.

User-Selected Gain Adjustment: The illustrative configuration of components of scanner system 150A shown in FIG. 8, and GUI 782A shown in FIG. 9, address the problem of emission signal saturation based either on user-selected gain adjustment or automatic gain adjustment. Illustrative implementations are now described with respect to FIGS. 10, 11, 12A, and 12B that are directed to the option of user-selected gain adjustment.

In this illustrative implementation, GUI 782A is employed to enable user 701 to vary emission detector control signal 784 over a first range of values and/or to vary variable gain element (VGA) control signal 783 over a second range of values, thereby controlling the gains of emission detector 415 and variable gain amplifier 815, respectively, during the scanning process (also referred to herein as a scanning operation). User 701 may determine that a gain adjustment is desirable by inspecting an image comprising scanned pixels, generated as described above with respect to FIGS. 6A–6D, for a previously conducted experiment similar to a new experiment, or a prior attempt at conducting the first experiment. User 701 may note that a significant portion of the previously scanned pixels in the prior experiment or prior attempt were uniformly and maximally bright (perhaps indicating saturation due to excessive scanner gain), that there are no maximally bright pixels (perhaps indicating that a low gain setting has resulted in a less-than-attainable dynamic range), or that there are a significant number of dark pixels (again perhaps indicating less-than-attainable dynamic range). Alternatively, during the previously conducted scan, executable 790' may have counted the number of pixels having digital voltage values represented by maximum digital voltage line 672. If this number exceeded either a predetermined or user-selected threshold, executable 790' could have provided an appropriate message to user 701 through a graphical user interface or another conventional technique. Similarly, executable 790' may have counted the number of dark pixels to determine, for example, if the proportion of dark pixels exceeds an anticipated threshold. In any of these cases, user 701 may decrease the gain to avoid saturation or increase the gain to improve resolution of small signals for future scanning operations. These, and other, optional operations by executable 790' are described below in relation to implementations including automatic gain adjustment.

More generally, user 701 may determine the desired gain based on a variety of additional factors, such as experience with scanner 160A, experience with the fluorescent labels in particular dyes to be used, and so on. By rescanning multiple times at a series of gain settings, user 701 may obtain measures of pixel intensities across a range that exceeds the dynamic range of the scanner. For one example of how extended dynamic range may be determined, see U.S. Pat. No. 6,171,793, hereby incorporated by reference herein for all purposes.

Figure 9:
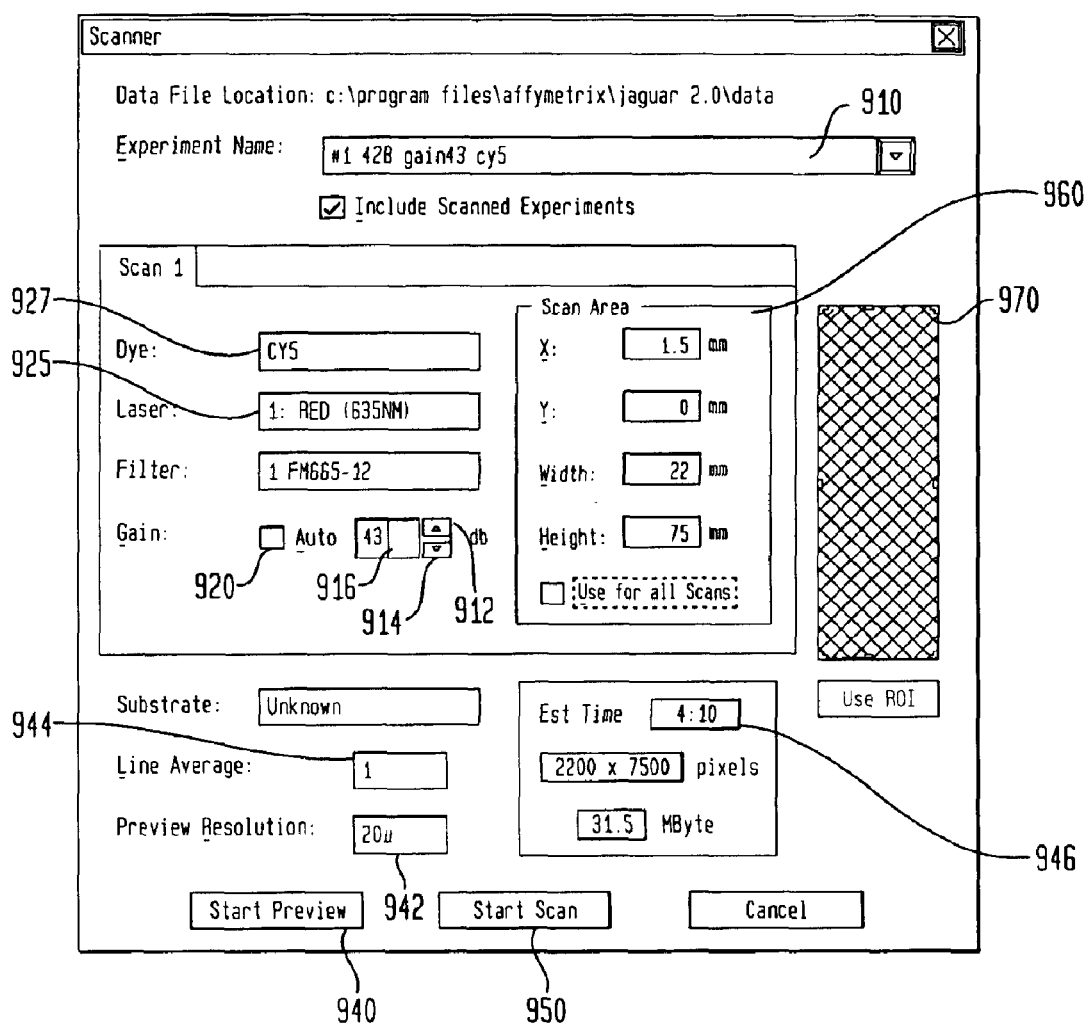
FIG. 9 is a graphical representation of one embodiment of a graphical user interface of the gain adjustment systems of FIG. 8.

FIG. 9 is a graphical representation of one of many possible implementations of GUI 782A. GUI 782A includes up-arrow and down-arrow graphical elements 912 and 914 that, in accordance with known techniques, enable user 701 to respectively increase or decrease a value displayed in graphical element 910. For example, user 701 may illustratively be assumed to be enabled to vary the value displayed in element 916 between 0 and 70, wherein the selected value represents a decibel (dB) value within this range. In this manner, user 701 may set a gain in relation to a reference gain at which scanner 160A nominally operates, i.e., operates when the user-selected gain value is zero.

The reference gain in this example is illustratively assumed to be set by the maker of scanner 160A in accordance with various objectives. One objective may be to ensure that the reference gain is sufficiently low that saturation will not occur at that level. Thus, user 701 may be presented simply with the option of increasing gain in order to more accurately identify low-intensity emissions and need not be concerned with saturation if the user-selected gain value remains at zero. In alternative implementations, the reference gain may be set higher and the user provided with options for decreasing, as well as increasing, the gain of scanner 160A in relation to that reference.

Another objective that may be relevant to establishing the reference gain is to calibrate scanner 160A with other scanners. For example, a technician may adjust the reference gain based on scanning a benchmark fluorescent feature on a calibration slide. The technician measures the value of emission signal 492 when the benchmark is excited and adjusts the gain of emission detector 415 so that signal 492 is a standard value. As noted, this standard value is low enough to ensure that saturation will not occur if the user-selected gain value remains at a default value of zero. This procedure typically is repeated for each of excitation sources 420 because the response of emission detector 415 may vary depending on the wavelength of filtered emission beam 454.

Figure 10:
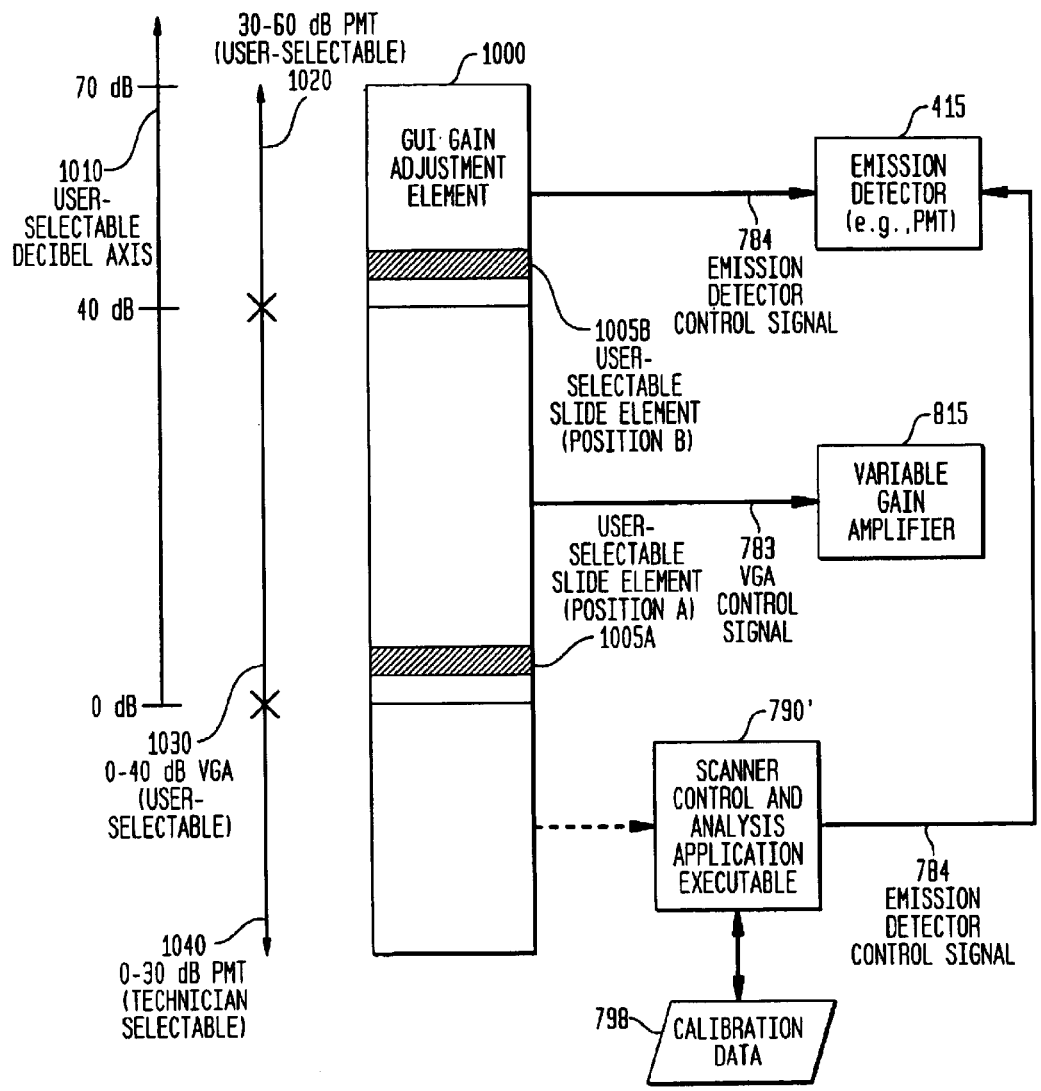
FIG. 10 is a graphical representation of one embodiment of a distribution of calibration and user-selected gain controls applied to an emission detector and a variable gain element of the gain adjustment systems of FIG. 8.

In the illustrated implementation, it is illustratively assumed that the gain of emission detector 415 may be varied over a range of 60 decibels by varying a control voltage (shown in FIG. 8 as emission detector control signal 784). It is further illustratively assumed that up to 30 decibels is reserved for making the calibration. That is, even if the calibration requires an increase of 30 decibels in emission signal 492, a range of an additional 30 decibels will be available for user-selected adjustment of signal 492. FIG. 10 is a graphical representation of an illustrative distribution of both calibration and user-selected gain settings as applied to emission detector 415 and variable gain amplifier 815. As shown in FIG. 10, executable 790' stores the calibrated gain settings for each of excitation sources 420 in a memory unit of computer 100B, as illustratively represented by calibration data 798 in system memory 720 of the present example. For instance, data 798 may include records specifying that the calibration setting for detector 415 when source 420A (e.g., diode laser) is operational is 15 decibels, and the calibration setting for detector 415 when source 420B (e.g., doubled YAG laser) is operational is 5 decibels. These functions are indicated in FIG. 10 by the dotted line showing the correspondence between calibration range 1040 (30 dB in this example) and executable 790', and the transfer of the calibration control value from data 798 via executable 790' and emission detector control signal 784 to emission detector 415.

In a specific illustrative implementation, a gain value, as selected by user 701 using graphical elements 912 or 914 and displayed in element 910, is provided to executable 790' in accordance with known GUI techniques. User 701 typically may wish to select a gain value that is specific to the particular one of excitation sources 420 used to generate emission signal 492. This option is desirable because, as noted, the response of emission detector 415 may vary depending on the wavelength of emission signal 492 that, in turn, generally depends on the wavelength of the excitation signal generated by the excitation source. Other experimental parameters, such as the type of label (e.g., fluorophore dye), may similarly influence user 701''s selection of gain. In the example shown in FIG. 9, user 701 has determined that for a scanning operation related to a particular experiment identified in graphical element 910, in which the dye CY5 (see graphical element 927) may have been associated with hybridized probe-target pairs of one of arrays 132, and in which the array is to be excited by red diode laser 420A (see graphical element 925), the user-selected gain should be 43 decibels (see graphical element 916). User 701 could similarly specify that, in the same scanning operation, another dye is also potentially present and that another one of sources 420 is to be used (in the same or sequential scan, depending on the design of scanner 160A) to excite the fluorophores of this dye, if present.

It is now illustratively assumed that user 701 instructs executable 790' to cause scanner 160A to scan an array in a scanning operation undertaken in accordance with the experiment represented in FIG. 9. Executable 790' causes digital signals to be generated that represents the user-selected gain values for the specified excitation sources, and these signals are provided to a digital-to-analog converter (not shown) that provides analog control signals representative of the user-selected gain values, all in accordance with any of a variety of known techniques. For a gain value between zero and 40 decibels in the illustrated implementation, executable 790' causes switching to be enabled such that the representative analog value (e.g., VGA control signal 783) is provided to a control input of variable gain element (VGA) 815. Thus, for instance, user 701 may select a gain of 5 decibels by manipulating elements 912 or 914 as described above or, in an alternative implementation of aspects of GUI 782A shown in FIG. 10, placing user-selectable slide element 1005 to a first position A as represented by element 1005A. The result in either case is that a control voltage is applied to VGA 815 such that, in accordance with known techniques, amplified analog emission signal 817 is increased by 5 decibels over a nominal operating gain (e.g., unity) for VGA 815. In this illustrative range of zero to 40 decibels, no portion of the user-selected gain is allocated to emission detector 415; i.e., all of the user-selected gain is allocated to VGA 815. Thus, the portion of user-selected gain allocated to emission detector 415 may hereafter be referred to as a no-change value to indicate that, although the gain of emission detector 415 may have been adjusted for purposes of calibration or for other reasons, it is not adjusted based on the user-selected gain in this example.

For user-selected gain values of 40 decibels and above in the illustrated implementation, executable 790' maintains emission detector control signal 784 such that the output of VGA 815, i.e., emission signal 817, is increased by 40 decibels above its nominal 0 dB level. Executable 790' also causes emission detector control signal 784 to assume a value representative of the amount that the user-selected value exceeds 40 decibels. For instance, if user 701 selects 45 dB, as represented by user-selectable slide element 1005B, VGA control signal 783 is set at a value such that VGA 815 provides 40 decibels of gain, and emission detector control signal 784 assumes a value such that emission detector 415 provides an additional 5 decibels of gain.

It will be understood that many other techniques are available by which user 701 may select a desired gain and by which a portion of this gain may be implemented by emission detector 415 and a portion by variable gain amplifier 815. For example, the initial range of gain could be implemented by emission detector 415 rather than by VGA 815 as in the illustrated example. Also, any user-selected gain could be implemented in a same range in any proportion between emission detector 415 and VGA 815. For example, any gain selected by user 701 could be implemented 50% by emission detector 415 and 50% by VGA 815. Further, in some implementations, any available capacity in calibration range 1040 (e.g., if scanner 160A were calibrated at 20 decibels so that 10 decibels of the 30 decibels in range 1040 were available) could be provided for user-selected gain so that, in the illustrated example, user-selectable range of gain values 1020 could be increased from 30 decibels to 40 decibels. Also, many alternative user interfaces may be used. For example, GUI gain adjustment element 1000 was described above as having a single user selectable slide element 1005 that could be moved by user 701 between various positions such as positions A and B of the illustrated example. In one of many alternative implementations, two slide elements could be provided so that user 701 could separately select a gain attributed specifically to emission detector 784 (e.g., a separate slide element 1005B operating over a range of gain values 1020) and a gain attributed specifically to VGA 815 (e.g., a separate slide element 1005A operating over a separate range of gain values 1030). In this alternative implementation, gain ranges 1020 and 1030 could, of course, be separated from each other rather than stacked.

Figure 11:
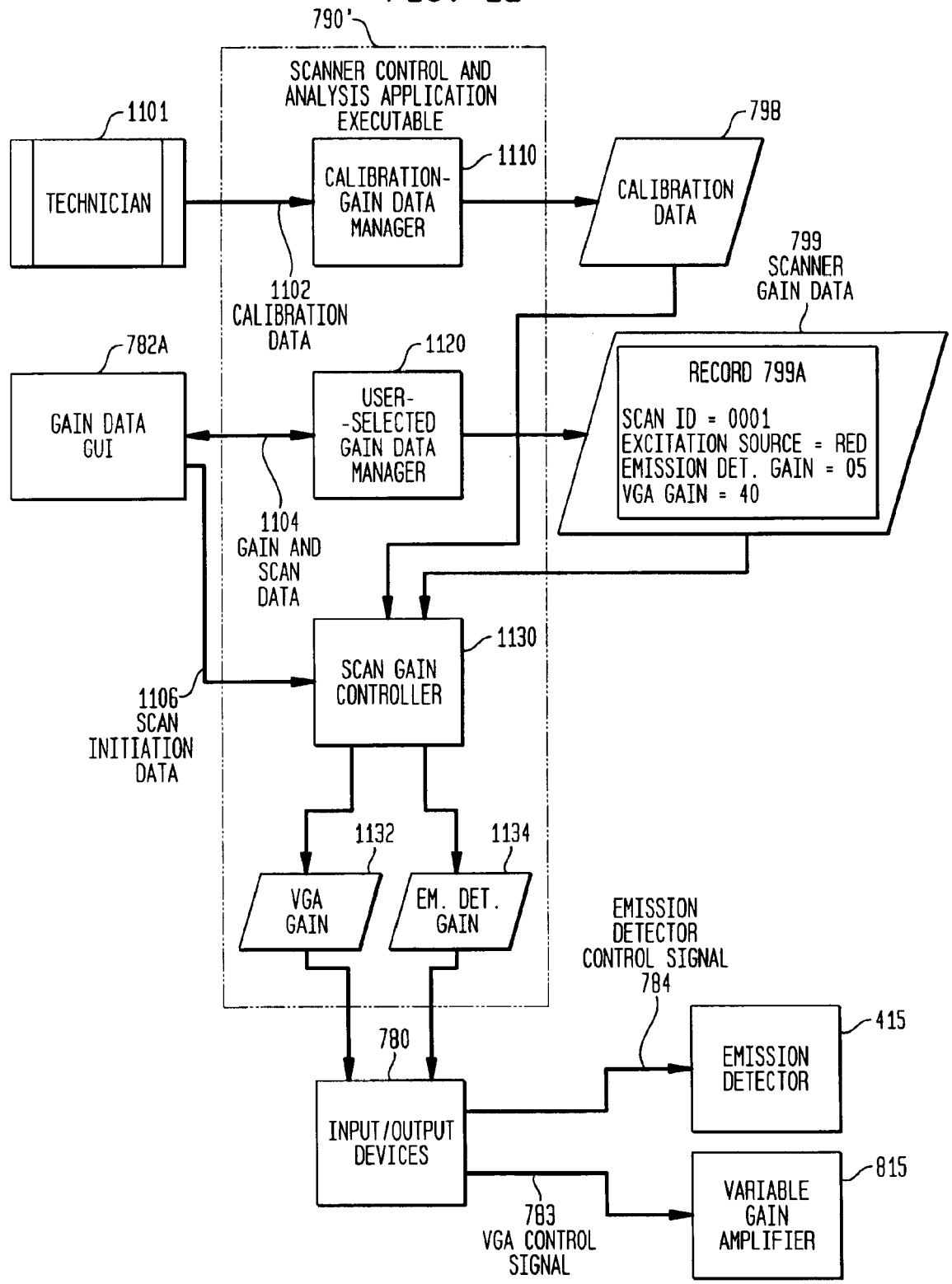
FIG. 11 is a functional block diagram of one embodiment of a scanner control and analysis application of the gain adjustment systems of FIG. 8.
Figure 12A:
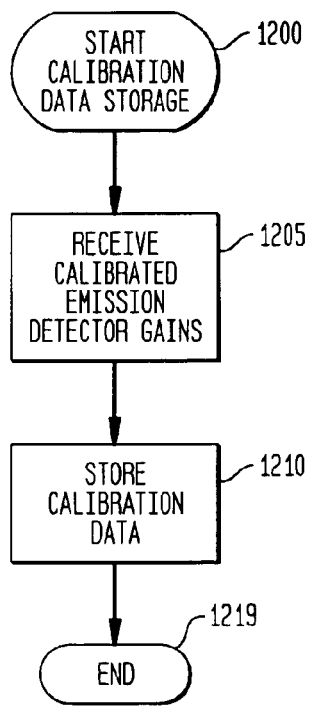
FIGS. 12A, 12B, and 12C are flow charts of illustrative method steps for respectively storing calibration gain data, storing user-selected gain data, and implementing calibration and user-selected gain adjustments.
Figure 12B:
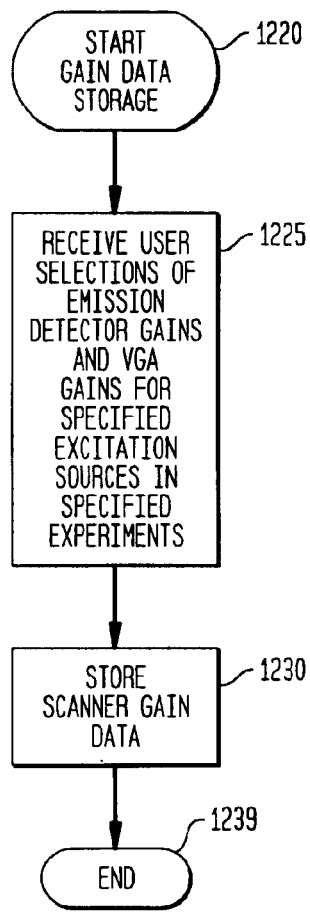
Figure 12C:
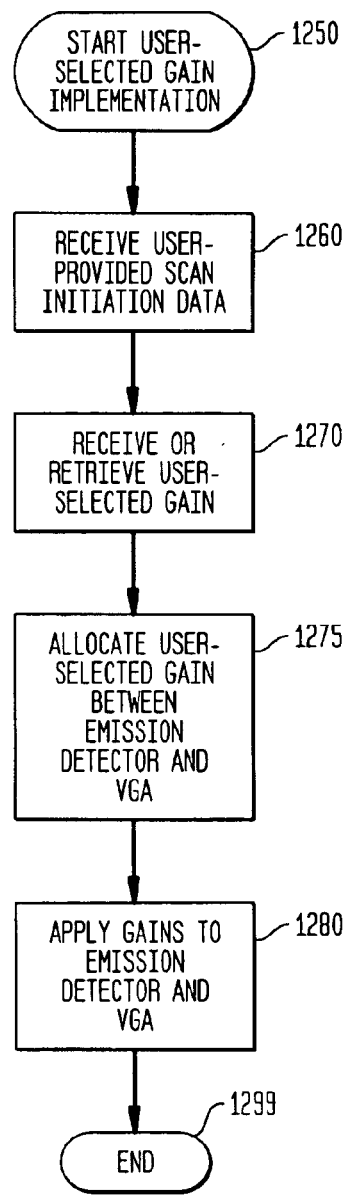

FIG. 11 is a functional block diagram including elements of application executable 790' that implement some of the operations described above with respect to the illustrative example. FIGS. 12A–C are flow charts showing method steps corresponding to some of these operations. As shown in FIG. 11, application executable 790' includes calibration-gain data manager 1110 that receives calibration-gain data (i.e., values of calibrated gains for each of excitation sources 420) input by technician 1101 through an appropriate user interface (not shown). (See corresponding method step 1205.) Calibration-gain data manager 1110 stores this data in appropriate records or other data-storage formats of calibration data 798 so that a calibration gain is associated with each of excitation sources 420 (see step 1210).

Application executable 790' also includes user-selected gain data manager 1120 that receives the user-selected gain to be applied to emission detector 415 and VGA 815. This gain may input via GUI 782A of FIG. 8, or alternative interfaces such as that employing graphical elements 912 and 914 or user-selectable slide element 1005. The user-selected gain typically is associated by user 701 with particular ones of excitation sources 420 and/or particular experiments in which, for example, certain dyes with fluorescent labels are to be used. (See corresponding method step 1225.) Thus, user 701 may repeatedly use GUI 782A, or another interface, to select a gain to be used for particular excitation sources and/or experiments. User-selected gain data manager 1120 stores this data in appropriate records or other data-storage formats of scanner gain data 799 so that a user-selected gain is associated with each of excitation sources 420, typically for each of one or more specified experiments (see step 1230).

For example, an illustrative record 799A is shown that stores the information that, when a particular scan of a microarray experiment, identified as Scan ID=0001, is performed, emission signal 492 from red diode laser source 420A is to be amplified by 45 decibels by providing a gain of 5 decibels from emission detector 415 and 40 decibels from VGA 815. It is illustratively assumed that user 701 directs scanner 160A to perform scan 0001 by using an interface such as illustrative GUI 782A that is graphically represented in FIG. 9 (see step 1260 and graphical elements 940 or 950, described below).

Application executable 790' includes scan gain controller 1130 that, in accordance with any of a variety of known data search and retrieval techniques, retrieves record 799A. Alternatively, rather than storing scanner gain data 799 and later initiating a scan, user 701 may specify scanner gain data 799 and provide scan initiation data 1106 using a common user interface and/or in a common operation in accordance with other known techniques. (See step 1270.) Scan initiation data 1106 typically includes an indicator that user 701 has initiated a scan or a preview scan, such as may be done, for example, by selecting graphical elements 950 or 940, respectively. Also, initiation data 1106 may include other information such as a selected preview resolution, described below.

Based on scanner gain data 799, scan gain manager 1130 allocates the user-selected gain value between emission detector 415 and VGA 815 (see step 1275). Scan gain manager 1130 then applies these gains by, for example, causing emission detector control signal 784 to be sent to emission detector 415 to set its gain at 5 decibels and causing VGA control signal 783 to be sent to VGA 815 to set its gain at 40 decibels (see step 1280). Typically, these control signals are provided via a conventional output device of input/output devices 780 (see step 1280).

Automatic Gain Adjustment: User 701 also may choose to employ automatic gain adjustment rather than user-selected gain adjustment as just described. This choice may be implemented in accordance with a variety of known techniques, such as by user 701 selecting graphical element 920. Typically, this selection deactivates graphical elements for the implementation of user-selected gain (e.g., by graying out element 916 and deactivating elements 912 and 914). However, in some implementations, both options may be provided so that, for example, a user-selected gain value is used if the automatic gain adjustment technique is not able to function due to a lack of data or other reason. Also, automatic gain adjustment may be a default option, or it may be provided without providing the option of user-selected gain adjustment.

Figure 13:
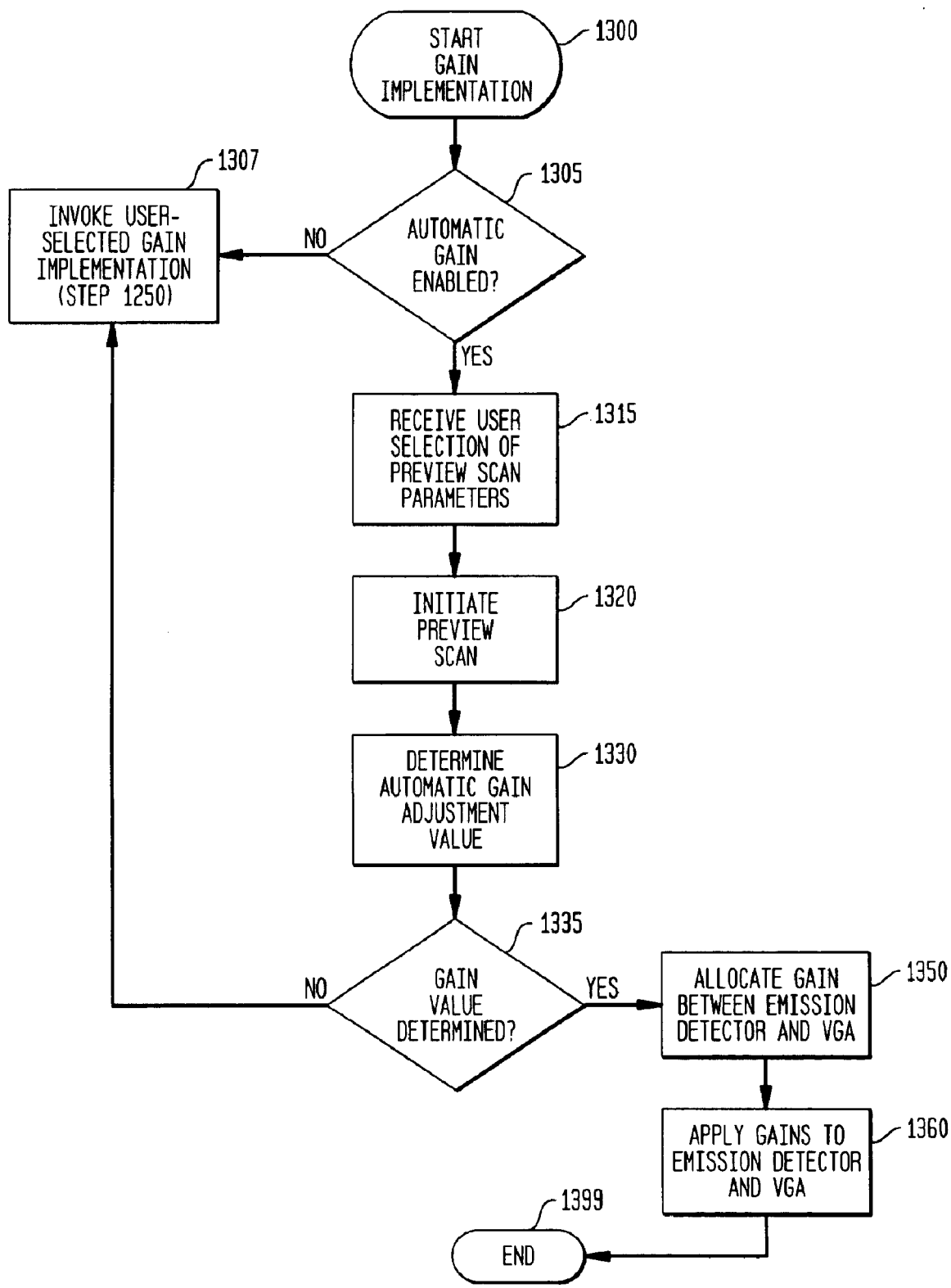
FIG. 13 is a flow chart of illustrative method steps by which the gain adjustment systems of FIG. 8 may determine, allocate, and apply gains.

FIG. 13 is a flow chart showing steps by which, in one illustrative embodiment, scan gain controller 1130 automatically determines a gain, allocates it between emission detector 415 and VGA 815, and applies it to those elements.

As indicated by method step 1305, controller 1130 in this example determines whether user 701 has enabled the automatic gain feature. If user 701 has not enabled the automatic gain feature, or it is de-selected by default or otherwise not enabled, a user-selected gain may be determined and allocated as described above (see step 1307, invoking step 1250).

If user 701 has enabled the automatic gain feature, user 701 in this example may also optionally provide parameters according to which a preview scan will be initiated by controller 1130 (see step 1315). Controller 1130 causes a preview scan to be made in order to obtain pixel intensity samples indicative of the range of pixel intensities in the scanned image (see step 1320).

To provide one of many possible examples of the implementation of steps 1315 and 1320, it is illustratively assumed that user 701 selects graphical element 942 (labeled Preview Resolution) to be 20 microns, as shown in GUI 782A of FIG. 9. Assuming, as above, a nominal pixel resolution of 10 microns, then this user selection is illustratively assumed to indicate that each group of two pixel values is averaged to provide a single sample pixel value. Thus, this user selection specifies a resolution parameter such that the resolution is 20 microns, or half the nominal resolution value. In alternative implementations, this user selection could indicate that only every other pixel is obtained or recorded, thus providing another sample measure for the same resolution.

It further is illustratively assumed in accordance with previous examples that translation stage 542 moves 10 microns in the y direction between each line scan. The user selection in this example of 20 micron pixel resolution may further be implemented by scanning every other line rather than every line, thus reducing the pixel resolution in the y direction also by half. Thus, for instance, in a regular scan mode, sample pixels are obtained both for scans 620 and successive scan 622 of the example of FIG. 6A. When user 701 selects 20 microns for the value of graphical element 942 indicating one half the nominal resolution, then, in this specific implementation, pixels from every other scan line, rather than every scan line, are included in the samples. Similarly, user 701 may select 50 micron resolution, resulting in this illustrative implementation in the averaging of every five 10-micron pixels in each scan line, and scanning only one-fifth as many lines in the y direction as would nominally be the case. That is, translation stage 542 is stepped five increments between scans, rather than the nominal one increment. As can be seen from FIG. 6A, at least two scan lines of sample pixels would be obtained from scanning probe 370A even if user 701 had elected to obtain sample pixels only from every fifth scan line, assuming that probe 370A is a spot of about 150 to 200 microns diameter, as is typical in some applications.

It will be understood that scanner 160A typically scans across many probes in each scan line. The scan line may extend from one edge of the substrate (e.g., microscope slide) to the other, or at least across the width of a portion of the substrate often referred to as a scanning area because within it are contained the features (i.e., in the present example, probes or probe-target pairs, sometimes therefore referred to as probe features) to be scanned. The locations on the substrate where probe features are located may therefore be referred to herein as probe-feature locations. Similarly, translation stage 542 typically is moved a sufficient distance in the y direction so that the full height of the scanning area is scanned. In the illustrated example of GUI 782A of FIG. 9, user 701 may define the scanning area by selecting values in a graphical portion 960 (labeled Scan Area). For example, a value for X in portion 960 indicates a distance in the x direction from the left edge of the slide to the left edge of the scanning area, a value for Y in portion 960 indicates a distance in the y direction down from the top edge of the slide to the top edge of the illustrative rectangular scanning area, and the Width and Height values in portion 960 specify the width and height of the illustratively rectangular scanning area. Alternatively, user 701 may employ conventional drag or other techniques to change the dimensions of the scanning area as represented by the rectangular graphical element 970 of this example. It will be understood that the scanning area need not be a rectangle in other implementations, but may be any shape.

Figure 14:
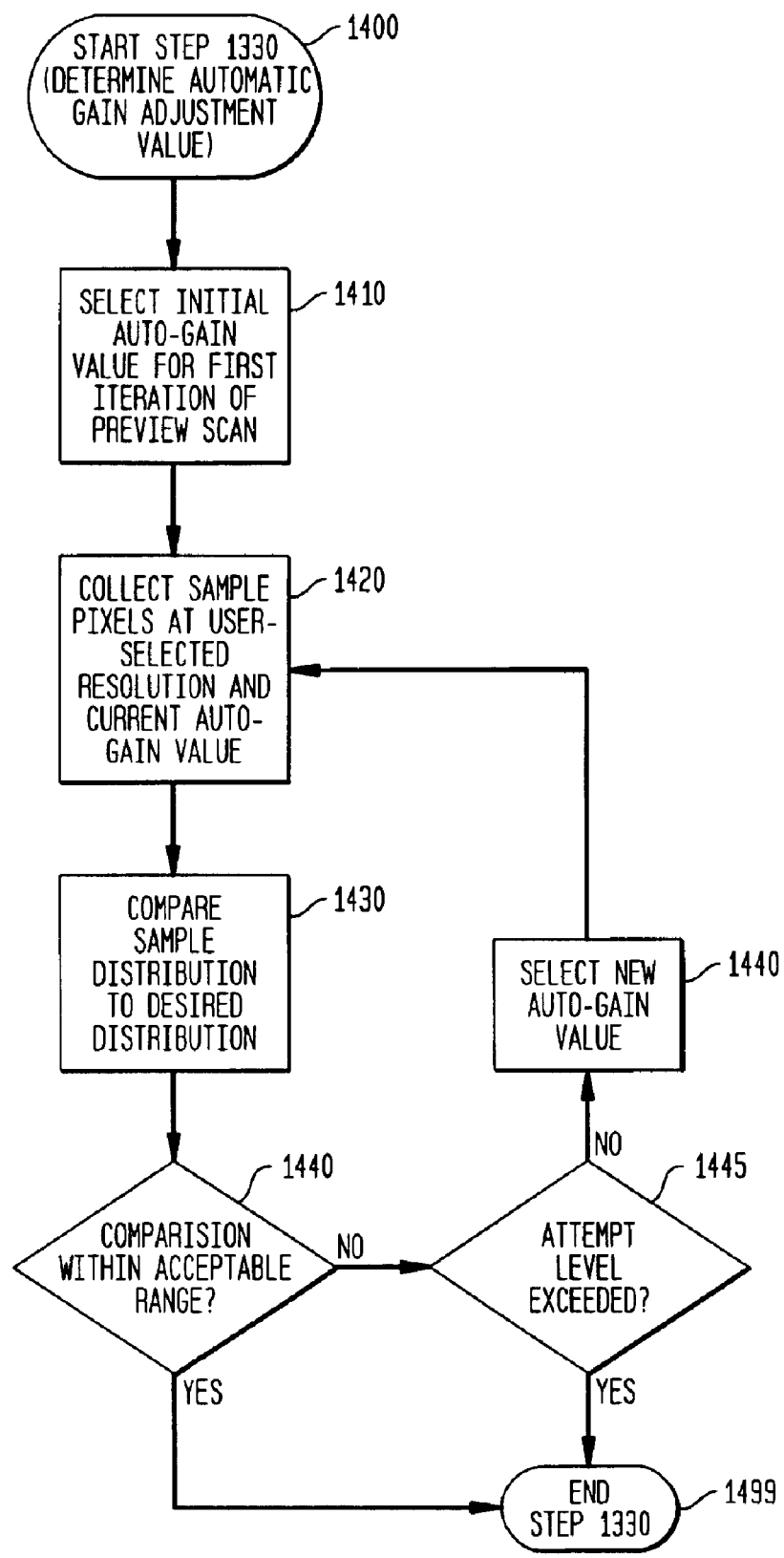
FIG. 14 is a flow chart showing in greater detail illustrative method steps directed to determining an automatic gain adjustment value, as generally shown in FIG. 13.
Figure 15:
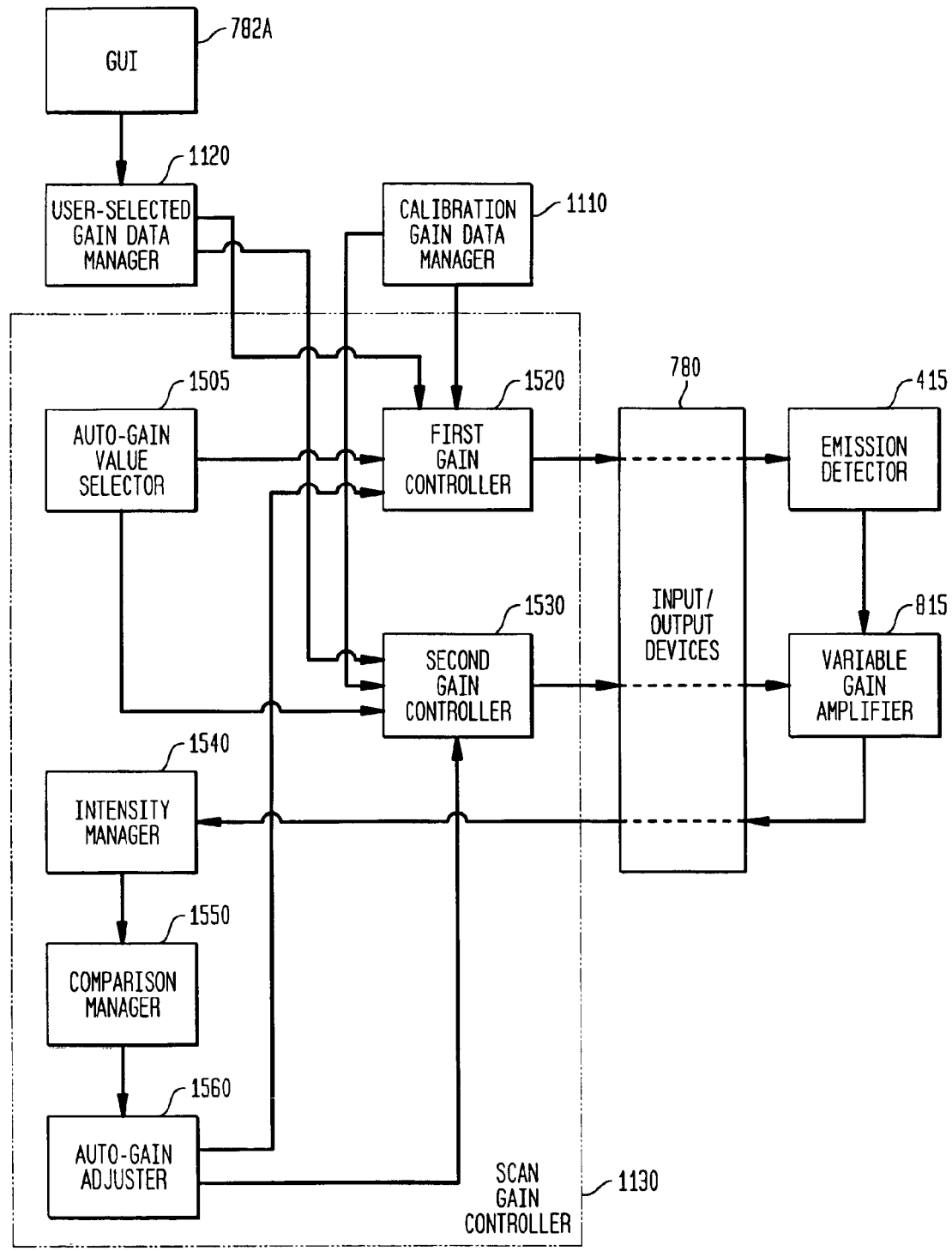
FIG. 15 is a functional block diagram of one embodiment of a scan gain controller by which the gain adjustment systems of FIG. 8 may automatically determine, allocate, and apply gains.

Controller 1130 may store the sample pixel intensity values collected during the preview scan over the scanning area in an appropriate data structure, such as represented by sample intensity data 797 stored in system memory 720 as shown in FIG. 7. Based on these sample values, controller 1130 determines a value for the automatic gain adjustment (see step 1330). This determination may be made in a variety of ways. One illustrative technique is represented by the flow chart of FIG. 14 and the functional block diagram of FIG. 15. As shown in step 1410, controller 1130 determines an initial auto-gain value for a first iteration of the preview scan (see auto-gain value selector 1505). For instance, using the present example of a 70 decibel range of gain achieved by a combination of gain from emission detector 815 and gain from VGA 415, controller 1130 may select an initial gain at the mid-point of this range, i.e., 35 decibels, although any other initial value may be selected in other implementations. Controller 1130 may, but need not, allocate this 35 decibels of gain between emission detector 815 and VGA 415 in the same manner as described above with respect to the allocation of user-selected gain. Thus, in the illustrated example in which the first 40 decibels is allocated to VGA 415 (above the calibration gain allocated to emission detector 815), the 35 decibels would all be allocated to VGA 415. As indicated by step 1420 and described above, sample pixels are then collected for the scanning area at the user-selected resolution and with the initial value of auto gain selected by controller 1130 (see intensity manager 1540).

Controller 1130 then compares the distribution of sample pixel intensities to a desired distribution (see comparison manager 1550). This comparison may be accomplished in accordance with any of a wide variety of statistical and other techniques. In some applications, a statistical measure, such as a mean or average, may be calculated and compared with a desired mean or average intensity. Generally, however, such an approach would not necessarily take into account the characteristics of a typical scan in which, for example, the number of background pixels, i.e., pixels associated with a dark background (i.e., no fluorescent probe-target features possible since probes were not deposited) are relatively large and relatively predictable. Thus, it typically is advantageous to devise a comparison technique that takes into account expected relationships of low intensity (hereafter sometimes referred to for convenience as dark) pixels to high intensity (light) pixels, including the expected relationship of background pixels to probe pixels, i.e. pixels associated with probes that may be associated with fluorescent labels or other emission labels.

As but one non-limiting example of a technique that accounts for anticipated scan characteristics, controller 1130 may assign each pixel intensity value to a bin of a histogram. As in the example of digital conversion range 662 of FIG. 6C, the possible digital range of these pixel intensity values in this illustration is between 0 and 65,535. Thus, for instance, 15 bins may be used wherein bins 1 through 5 contain the lower intensity values (where pixels of intensity value 0 are assigned to bin 1), bins 6 through 10 contain mid-range intensity values, and bins 11 through 15 contain high-range intensity values (where pixels of intensity value 65,535 are assigned to bin 15).

Controller 1130 calculates in this specific illustrative example a ratio determined by dividing the number of pixel intensity values in the mid-range bins by the number of pixel intensity values in the high-range bins. If this ratio is equal to or greater than 2.0, then the auto-gain used to conduct the preview scan is deemed to be satisfactory. This determination, as indicated, may be based on empirical data from successful scans under various conditions of dyes, excitation sources, and other factors; on knowledge of expected ratios of background pixels to probe pixels; on knowledge of expected intensity ranges of fluorescent signals; and/or other considerations. Various other tests or comparisons may be applied. For example, if the number of intensity values in bin 15 is above some threshold expected value, then it may be concluded that saturation has occurred and that the auto gain used in the preview scan was too high. Similarly, a high number of intensity values in bin 1 may indicate that the auto gain was set too low. Many varieties and combinations of such tests and comparisons will now be appreciated by those of ordinary skill in the relevant art based on the present description.

If the ratio mentioned above is less than 2.0 in this specific example, controller 1130 concludes that the auto gain used for the preview scan was too high, thus resulting in a greater than desired or expected number of intensity values in the high-range bins. Alternatively, as noted in one of many alternative or additional tests, controller 1130 may draw the same conclusion based on the number of intensity values in the high-range bins. In any event, it is now illustratively assumed that controller 1130 determines that the actual distribution of intensity values did not conform to the expected or desired intensity value distribution because of a surplus of light pixels (see no exit from decision element 1440). Controller 1130 then reduces the auto gain in accordance with any of a variety of techniques (see step 1440). For example, controller 1130 may reduce the gain by one-half, i.e., to 35 dB–6 dB=29 decibels in an illustrative specific, non-limiting, example. Another preview scan may then be done (see step 1420) using the revised auto gain of 29 decibels. If controller 1130 determines that this gain also is too high, then this value may be reduced by about one-half, i.e., to 29 dB–6 dB=23 decibels, and this new auto-gain value used in another preview scan.

Similarly, if the ratio mentioned above exceeds the target ratio value of about 2.0 in this specific example by a threshold amount (e.g., if the ratio is 4.0 or above), controller 1130 may concludes that the auto gain used for the preview scan was too low, thus resulting in a greater than desired or expected number of intensity values in the mid- (and/or low-) range bins. Alternatively, as noted, controller 1130 may draw the same conclusion based on the number of intensity values in the mid- or low-range bins. In any of these cases, controller 1130 consequently increases the auto gain in accordance with any of a variety of techniques (see step 1440 and auto-gain adjuster 1560). For example, controller 1130 may increase the gain by a factor of two, i.e., to 35 dB+6 dB=41 decibels in the illustrative example. Another preview scan may then be done (see step 1420) using the revised auto gain of 41 decibels. If controller 1130 determines that this gain also is too low, then this value may be further increased by another factor of two, and so on. If the new gain is too high, then it may be decreased based on any of a variety of measures of the difference between it and the previous gain, e.g., from 41 decibels to 41 dB−3 dB=38 decibels. This process may be repeated a predetermined number of times, a number of times selected by user 701, or a number of times computed based on the likelihood of finding a value that meets all tests (see decision element 1445).

It is now illustratively assumed that controller 1130 succeeds in determining an acceptable automatic gain adjustment value (see decision element 1335). Controller 1130 may notify user 701 in accordance with known techniques that a gain value has been determined so that user 701 may initiate a scan at nominal resolution (e.g., by selecting start scan graphical element 950) using the automatically determined gain value. Alternatively, controller 1130 may automatically initiate a scan at nominal resolution using the automatically determined gain.

In the illustrated implementation, controller 1130 allocates a portion of the automatically determined gain value to be applied to emission detector 815 and a portion to be applied to VGA 815 (see step 1350). As in the case of user-selected gains, these apportioned gains typically are applied via an output device of input/output devices 780 (see step 1360). If controller 1130 is not able to automatically determine a gain value, user 701 may be given the opportunity to select a gain value (see element 1337 and step 1307). Alternatively, controller 1130 may notify user 701 of the situation and/or initiate a full resolution scan using the gain value that provided the closest match with the desired pixel distribution.

Having described various embodiments and implementations of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element.

For example, for purposes of clarity the functions of computer 100B and scanner 160A are described as being implemented by the functional elements shown in FIG. 8. However, aspects of the invention need not be divided into these distinct functional elements. Similarly, operations of a particular functional element that are described separately for convenience need not be carried out separately. For example, some or all of the functions of CPLD 830 could be implemented by process controller 740, and vice versa. Similarly, in some embodiments, any functional element may perform fewer, or different, operations than those described with respect to the illustrated embodiment. Also, functional elements shown as distinct for purposes of illustration may be incorporated within other functional elements in a particular implementation. For example, filters 810 and/or 820 may be components of amplifier 815, although they are shown separately in FIG. 8 for purposes of illustration. Also, a user may provide gain and scan data at the same time as scan initiation data.

Also, the sequencing of functions or portions of functions generally may be altered. For example, the method steps shown in FIGS. 12A–C and 13 generally need not be carried out in the order suggested by the figures. Among many possible examples, the steps and decision elements of FIG. 13 could be included in FIG. 112C, steps 1350 and 1360 could be combined or carried out in parallel, and so on.

In addition, it will be understood by those skilled in the relevant art that control and data flows between and among functional elements of the invention and various data structures may vary in many ways from the control and data flows described above. More particularly, intermediary functional elements (not shown) may direct control or data flows, and the functions of various elements may be combined, divided, or otherwise rearranged to allow parallel processing or for other reasons. Also, intermediate data structures or files may be used, various described data structures or files may be combined, the sequencing of functions or portions of functions generally may be altered, and so on. Numerous other embodiments, and modifications thereof, are contemplated as falling within the scope of the present invention as defined by appended claims and equivalents thereto.

What is claimed is:

1. A computer program product for adjusting the gun of a scanner having one or more excitation sources, an emission detector having a first gain, and a variable gain element having a second gain, wherein the computer program product, when executed on a computer system, performs a method comprising the steps of:

(a) providing a first user interface constructed and arranged to enable a user to select a user-selected gain value;
    (b) receiving the user-selected gain value,
    (c) adjusting the first gain based, at least in part, on a first portion of the user-selected gain value; and
    (d) adjusting the second gain based, at least in part, on a second portion of the user-selected gain value.

2. The computer program product of claim 1, wherein:

step (c) includes the steps of
        (i) determining the first portion to be equal to a no-change value when the user-selected gain value is equal to or less than a threshold value, and
        (ii) determining the first portion to be equal to an excess of the user-selected gain value over the threshold value, when the user-selected gain value is greater than the threshold value; and step (d) includes the steps of
        (i) determining the second portion to be equal to the user-selected gain value when the user-selected gain value is equal to or less than a threshold value, and
        (ii) determining the second portion to be equal to the threshold value when the user-selected gain value is equal to or greater than the threshold value.

3. The computer program product of claim 2, wherein:

the threshold value is predetermined.

4. The computer program product of claim 1, wherein:
step (c) includes the steps of
  (i) determining the first portion to be equal to the user-selected gain value when the user-selected gain value is equal to or less than a threshold value, and
  (ii) determining the first portion to be equal to the threshold value when the user-selected gain value is equal to or greater than the threshold value: and
step d) includes the steps of
  (i) determining the second portion to be equal to a no-change value when the user-selected gain value is equal to or less than a threshold value, and
  (ii) determining the second portion to be equal to an excess of the user-selected gain value over die threshold value, when the user-selected gain value is greater than the threshold value.

5. The computer program product of claim 4, wherein:
the threshold value is predetermined.

6. The computer program product of claim 1, wherein the method further comprises the step of:
  (e) receiving a calibration gain for a first of the one or more excitation sources, wherein the calibration gain is based, at least in part, on an output of the emission detector responsive to the first excitation source exciting a calibration source; and
  (f) adjusting the first gain, the second gain, or both based, at lent in part, on the calibration gain.

7. The computer program product of claim 6, wherein:
the calibration gain is based on a measurement that depends, at least in part, on the output of the emission detector.

8. The computer program product of claim 1, wherein:
the first user interface further is constructed and arranged to enable the user to associate the user-selected gain value with a first of the one or more excitation sources;
step (b) further includes receiving from the first user interface the association of the user-selected gain value with the first excitation source; and
steps (c) and (d) are done when the first excitation source is operational.

9. The computer program product of claim 8, wherein:
the user associates the user-selected gain value with the first excitation source based, at least in part, on identifying a scanning operation in which the first excitation source is operational.

10. The computer program product of claim 1, wherein:
the first user interface further is constructed and arranged to enable the user to associate the user-selected gain value with a first of one or more emission labels;
step (b) further includes receiving from the first user interface the association of the user-selected gain value with the first emission label; and
steps (c) and (d) are done when the first emission label is excited in a scanning operation.

11. The computer program product of claim 1, wherein:
the method further comprises the step of
  (e) providing a second user interface constructed and arranged to enable a user to initiate a scanning operation; and
stop (b) further comprises the steps of
  (i) receiving the user-selected gain value from the first user interface and storing the user-selected gain value in a memory storage unit, and
  (ii) retrieving the user-selected gain value from the memory storage unit responsive to the user initiating a scanning operation.

12. The computer program product of claim 1, wherein:
the first and second user interfaces are included in a same user interface.

13. The computer program product of claim 1, wherein:
the emission detector includes a photomultiplier tube.

14. The computer program product of claim 1, wherein:
the first gain amplifies an emission signal based, at least in part, on emissions from an emission label spatially associated with a probe of a probe array.

15. The computer program product of claim 14, wherein:
the probe array is a spotted probe array.

16. The computer program product of claim 14, wherein:
the probe array is a synthesized probe array.

17. A computer program product for adjusting the gain of a scanner having one or more excitation sources, an emission detector having a first gain, and a variable gain element having a second gain, wherein the computer program product, when executed on a computer system, performs a method comprising the steps of:
  (a) receiving one or more user-selected gain values from one or more ranges of gain values;
  (b) adjusting the first gain based at least in part, on a first of the one or more user-selected gain values; and
  (c) adjusting the second gain based, at least in part, on a second of the one or more user-selected gain values.

18. The computer program product of claim 17, wherein the method further comprises the steps of:
  (d) receiving a calibration gain for a first of the one or more excitation sources, wherein the calibration gain is based, at least in part, on an output of the emission detector responsive to the first excitation source exciting a calibration source; and
  (e) adjusting the first gain, the second gain, or both based, at least in part, on the calibration gain.

19. The computer program product of claim 17, wherein:
the user interface further is constructed and arranged to enable the user to associate the first user-selected gain value with a first of the one or more excitation sources;
stop (a) further includes receiving from the user interface the association of the first user-selected gain value with the first excitation source; and
steps (b) and (c) are done when the first excitation source is operational.

20. A computer program product for adjusting the gain of a scanner having one or more excitation sources, an emission detector having a first gain, and a variable gain element having a second gain, wherein the computer program product, when executed on a computer system, performs a method comprising the steps of:
  (a) receiving a user-selected gain value;
  (b) adjusting the first gain based, at least in part, on a first portion of the user-selected gain value, including the steps of
    (i) determining the first portion to be equal to a no-change value when the user-selected gain value is equal to or less than a threshold value, and
    (ii) determining the first portion to be equal to an excess of the user-selected gain value over the threshold value, when the user-selected gain value is greater than the threshold value;
  (c) adjusting the second gain based, at least in part, on a second portion of the user-selected gain value;
  (d) receiving a calibration gain for a first of the one or more excitation sources, wherein the calibration gain is based, at least in part, on an output of the emission detector responsive to the first excitation source exciting a calibration source; and e) adjusting the first gain, the second gain, or both based, at least in part, on the calibration gain.

21. A gain adjustment system, comprising:
(a) a scanner having
  (i) one or more excitation sources,
  (ii) an emission detector having a fist gain, and
  (iii) a variable gain element having a second gain;
(b) a computer-implemented user interface constructed and arranged to enable a user to select a user-selected gain value; and
c) scanner control and analysis control logic comprising
  (i) a user-selected gain data manager constructed and arranged to receive the user-selected gain value, and
  (ii) a scan gain controller constructed and arranged to adjust the first gain based, at least in part, on a first portion of the user-selected gain value, and to adjust the second gain based, at least in part, on a second portion of the user-selected gain value.

22. The system of claim 21, wherein:
the scan gain controller further is constructed and arranged to determine the second portion to be equal to the user-selected gain value, and the first portion to be a no-change value, when the user-selected gain value is equal to or less than a threshold value; and to determine the second portion to be equal to the user-selected gain value, and the first portion to be equal to an excess of the user-selected gain value over the threshold value, when the user-selected gain value is greater than the threshold value.

23. The system of claim 21, wherein:
the scan gain controller further is constructed and arranged to determine the first portion to be equal to the user-selected gain value, and the second portion to be a no-change value, when the user-selected gain value is equal to or less than a threshold value; and to determine the first portion to be equal to the user-selected gain value, and the second portion to be equal to an excess of the user-selected gum value over the threshold value, when the user-selected gain value is greater than the threshold value.

24. The system of claim 21, wherein:
the scan gain controller further is constructed and arranged to receive a calibration gain for a first of the one or more excitation sources, wherein the calibration gain is based, at least in part, on an output of the emission detector responsive to the first excitation source exciting a calibration source; and to adjust the first gain, the second gain or both based, at least in part, on the calibration gain.

25. A method for adjusting the gain of a scanner having one or more excitation sources, an emission detector having a first gain, and a variable gain element having a second gain, comprising the steps of:
(a) receiving a user-selected gain value;
(b) adjusting the first gain based, at least in part, on a first portion of the user-selected gain value; and
(c) adjusting the second gain based, at least in part, on a second portion of the user-selected gain value.

26. The method of claim 25, wherein:
steps (b) and (c) include the step of allocating the user-selected gain between the flint and second portions based, at least in part, on one or more operational characteristics of the emission detector.

27. The method of claim 26, wherein:
the operational characteristics include signal to noise ratio.

28. A computer program product for adjusting the gain of a scanner having one or more excitation sources, an emission detector having a first gain, and a variable gain element having a second gain, wherein the computer program product, when executed on a computer system, performs a method comprising the steps of:
(a) selecting an auto-gain value;
(b) adjusting the first gain based, at least in part, on a first portion of the auto-gain value;
(c) adjusting the second gain based, at least in part, on a second portion of the auto-gain value;
(d) causing the scanner to collect a plurality of sample pixel intensity values using the adjusted first and second gains;
e) determining a comparison measure based on comparing one or more of the plurality of sample pixel intensity values to one or more of a plurality of desired pixel intensity values; and
(f) adjusting the auto-gain value based on the comparison measure.

29. The computer program product of claim 28, wherein;
steps (b) through (f) are repeated until the comparison measure reaches an acceptance value or range, or until a number of repetitions exceeds an attempt number.

30. The computer program product of claim 29, wherein:
the acceptance value or range, the attempt number, or both are user selected.

31. The computer program product of claim 29, wherein:
the acceptance value or range, the attempt number, or both are predetermined.

32. The computer program product of claim 29, wherein:
the acceptance value or range, the attempt number, or both are calculated.

33. The computer program product of claim 28, wherein:
the comparison measure includes a histogram of the plurality of sample pixel intensity values.

34. The computer program product of claim 33, wherein:
the comparison measure includes a ratio between a first portion of the plurality of sample pixel intensity values in a first number of bins of the histogram and a second portion of the plurality of sample pixel intensity values in a second number of bins of the histogram.

35. The computer program product of claim 28, wherein:
the comparison measure includes a statistical measure.

36. The computer program product of claim 35, wherein:
the statistical measure includes a mean or average of two or more of the plurality of sample pixel intensity values.

37. The computer program product of claim 28, wherein:
the first gain amplifies an emission signal based, at least in part, on emissions from an emission label spatially associated with a probe of a probe array; and 38. The computer program product of claim 37, wherein:
the probe array is a spotted probe array.

39. The computer program product of claim 37, wherein:
the probe array is a synthesized probe array.

40. The computer program product of claim 31, wherein:
the plurality of desired pixel intensity values is determined based, at least in part, on an expected ratio of background pixels on the probe array to probe pixels on the probe array.

41. The computer program product of claim 28, wherein:

step (b) includes the steps of
  (i) determining the first portion to be equal to a no-change value when the auto-gain value is equal to or less than a threshold value, and
  (ii) determining the first portion to be equal to an excess of the auto-gain value over the threshold value, when the auto-gain value is greater than the threshold value; and step (c) includes the steps of
  (i) determining the second portion to be equal to the auto-gain value when the auto-gain value is equal to or less than a threshold value, and
  (ii) determining the second portion to be equal to the threshold value when the auto-gain value is equal to or greater than the threshold value.

42. The computer program product of claim 41, wherein:

the threshold value is predetermined.

43. The computer program product of claim 28, wherein the method further comprises the step of:
  (g) receiving a calibration gain for a first of the one or more excitation sources, wherein the calibration gain is based, at least in part, on an output of the emission detector responsive to the first excitation source exciting a calibration source; and
  (h) adjusting the first gain, the second gain, or both based, at least in part, on the calibration gain.

44. The computer program product of claim 28, wherein:

the emission detector includes a photomultiplier tube.

45. A gain adjustment system, comprising:
  (a) a scanner having
    (i) one or more excitation sources,
    (ii) an emission detector having a first gain, and
    (iii) a variable gain element having a second gain; and
  (b) scanner control and analysis control logic comprising a scan gain controller constructed and arranged to
    (i) select an auto-gain value,
    (ii) adjust the first gain based, at least in part, on a first portion of the auto-gain value;
    (iii) adjust the second gain based, at least in part, on a second portion of the auto-gain value;
    (iv) cause the scanner to collect a plurality of sample pixel intensity values using the adjusted first and second gains;
    (v) determine a comparison measure based on comparing one or more of the plurality of sample pixel intensity values to one or more of a plurality of desired pixel intensity values; and
    (vi) adjust the auto-gain value based on the comparison measure.

46. A method for adjusting the gain of a scanner having one or more excitation sources, an emission detector having a first gain, and a variable gain element having a second gain, comprising the steps of:
  (a) selecting an auto-gain value;
  (b) adjusting the first gain based, at least in part, on a first portion of the auto-gain value,
  (c) adjusting the second gain based, at least in part, on a second portion of the auto-gain value;
  (d) causing the scanner to collect a plurality of sample pixel intensity values using the adjusted first and second gains;
  (e) determining a comparison measure based on comparing one or more of the plurality of sample pixel intensity values to one or more of a plurality of desired pixel Intensity values; and
  (f) adjusting the auto-gain value based on the comparison measure.

47. The method of claim 46, wherein:

steps (b) and (c) include the step of allocating the auto-gain between the first and second portions based, at least in part, an one or more operational characteristics of the emission detector.

48. The method of claim 47, wherein:

the operational characteristics include signal to noise ratio.

* * * * *